United States Patent [19]

Hölck et al.

[11] Patent Number: 4,963,686
[45] Date of Patent: Oct. 16, 1990

[54] CERTAIN PYRIDINOYLAMINO-INDOLIN-2-ONE DERIVATIVES

[75] Inventors: Jens-Peter Hölck, Mannheim; Alfred Mertens, Schriesheim; Wolfgang Kampe, Heddesheim; Bernd Müller-Beckmann, Grüstadt; Gisbert Sponer, Laudenbach; Klaus Strein, Hemsbach, all of Fed. Rep. of Germany

[73] Assignee: Boehringer Mannheim GmbH, Mannheim, Fed. Rep. of Germany

[21] Appl. No.: 217,143

[22] Filed: Jul. 5, 1988

Related U.S. Application Data

[60] Continuation of Ser. No. 12,098, Feb. 6, 1987, abandoned, which is a division of Ser. No. 731,500, May 7, 1985, Pat. No. 4,666,923.

[30] Foreign Application Priority Data

May 12, 1984 [DE] Fed. Rep. of Germany ....... 3417643
Dec. 20, 1984 [DE] Fed. Rep. of Germany ....... 3446417

[51] Int. Cl.$^5$ .................... C07D 401/12; A61K 31/44
[52] U.S. Cl. .................... 546/273; 546/262; 546/271; 548/411; 548/450; 548/484
[58] Field of Search .......................... 546/273

[56] References Cited

U.S. PATENT DOCUMENTS 4,696,931 6/1987 Hauel et al. .................. 514/261

FOREIGN PATENT DOCUMENTS 0098448 1/1984 European Pat. Off. ............ 544/333
0161632 11/1985 European Pat. Off. ............ 548/305
1529901 5/1968 France ........................ 548/486
1158532 7/1969 United Kingdom .............. 548/486
1206995 9/1970 United Kingdom .............. 548/486

OTHER PUBLICATIONS

"Über Derivate des m- und P-Phenylen-diamins sowie des 6-Amino-Oxindols," Paul Ruggle and Richard Grand, Helv. Chem. Acta. 20, 373–386 (1973).

*Primary Examiner*—Alan L. Rotman
*Attorney, Agent, or Firm*—Felfe & Lynch

[57] ABSTRACT

The new pyrrolobenzimidazoles according to the present invention are compounds of the general formula:

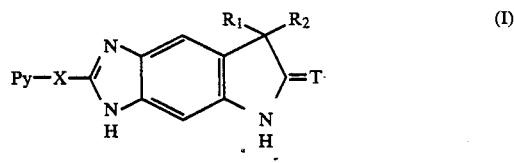

wherein $R_1$ is a hydrogen atom or an alkyl, alkenyl or cycloalkyl radical, $R_2$ is a hydrogen atom, an alkyl or alkenyl radical or a cyano group or a carbonyl group substituted by a hydroxyl or hydrazino group or by an alkyl, alkoxy, amino, alkylamino or dialkylamino group or together with $R_1$ represents a cycloalkylene radical or $R_1$ and $R_2$ together form an alkylidene or cycloalkylidene radical, X is a valency bond, a $C_1$-$C_4$ alkylene radical or a vinylene radical, T is an oxygen or sulphur atom and Py is a 2-, 3- or 4-pyridyl radical which optionally carries an oxygen atom on the ring heteroatom and/or can be substituted one or more times by alkyl, alkoxy, hydroxyl, cyano or nitro, as well as by halogen; the tautomers thereof and the physiologically acceptable salts thereof with inorganic and organic acids.

13 Claims, No Drawings

CERTAIN PYRIDINOYLAMINO-INDOLIN-2-ONE DERIVATIVES

This application is a continuation of U.S. Ser. No. 07/012,098 filed Feb. 6, 1987, now abandoned which is-turn is a division of U.S. Ser. No. 06/731,500 filed May 7, 1985, now U.S. Pat. No. 4,666,923.

The present invention is concerned with new pyrrolobenzimidazoles, with processes for the preparation thereof and with pharmaceutical compositions containing them.

Since the compounds of general formula I posses, when $R_1$ is not the same as $R_2$, an asymmetric carbon atom, the present invention also includes the optically-active forms and racemic mixtures of these compounds.

BACKGROUND OF THE INVENTION

The new compounds according to the present invention possess valuable pharmacological properties and, in particular, they increase the strength of the heart and/or have a blood pressure-lowering action and/or influence the thrombocyte aggregation and improve the microcirculation. They are therefore useful to treat coronary insufficiencies, cardiac failure, and blood circulatory disturbances and occlusive diseases.

In the general formulae given hereinafter and especially in the above-given general formula I, the substituents $R_1$ and $R_2$ can be the same or different and represent hydrogen atoms, straight-chained or branched alkyl or alkenyl radicals containing up to 6 or containing 2 to 6 carbon atoms, respectively, cyano groups or carbonyl groups substituted by hydroxyl, alkyl, alkoxy, amino, alkylamino, dialkylamino or hydrazino, each of the above-mentioned alkyl moieties being straight-chained or branched and containing up to 6 or 2 to 6 carbon atoms. However, hydrogen atoms and methyl, ethyl, allyl, cyano, carboxyl, acetyl, propionyl, methoxycarbonyl, ethoxycarbonyl, aminocarbonyl, methylaminocarbonyl, dimethylaminocarbonyl and hydrazinocarbonyl groups are especially preferred for $R_1$ and $R_2$.

If only $R_2$ represents a hydrogen atom, then $R_1$ is a straight-chained alkyl radical containing up to 6 carbon atoms or a branched alkyl radical, a cycloalkyl or alkenyl radical containing 3 to 7 carbon atoms, a cyano group or a carbonyl group substituted by alkyl, alkoxy, amino, alkylamino, dialkylamino or hydrazino group. Preferred in this sense are methyl, ethyl, isopropyl, isobutyl, pentyl, cyclopentyl, cyclohexyl, allyl, cyano, acetyl, propionyl, methoxycarbonyl, ethoxycarbonyl, aminocarbonyl, methylaminocarbonyl, dimethylaminocarbonyl and hydrazinocarbonyl.

$R_1$ and $R_2$, together with the carbon atom to which they are attached, can also form a cycloalkyl ring containing 3 to 8 carbon atoms which is preferably a spirocyclopropyl, spirocyclobutyl, spirocyclopentyl or spirocyclohexyl radical.

$R_1$ and $R_2$ can together also form a $C_2$–$C_6$ alkylidene or $C_3$–$C_8$ cycloalkylidene radical, the isopropylidene radical thereby being preferred.

Alkyl and alkoxy substituents of the pyridine ring can contain up to 6 and preferably up to 4 carbon atoms, methyl, ethyl, methoxy and ethoxy radicals being preferred. halogen is to be understood to be fluorine, chlorine or bromine, chlorine being preferred.

When Py is a 2-, 3- or 4-pyridyl radical which optionally carries an oxygen atom on the ring heteroatom and/or can be substituted by one or more times by alkyl, alkoxy, hydroxyl, cyano or nitro, as well as by halogen, and x is a valency bond, then Py is preferably a 2-pyridyl, 2-(N-oxypyridyl), 2-(5-n-butylpyridyl), 3-pyridyl, 3-(N-oxypyridyl), 3-(6-methylpyridyl), 3-(6-cyanopyridyl), 3-(6-nitropyridyl), 3-(6-hydroxypyridyl), 3-(2-methoxy-6-methylpyridyl), 4-pyridyl, 4-(N-oxypyridyl), 4-(2-methylpyridyl), 4-(2-ethylpyridyl), 4-(2-hydroxypyridyl), 4-(2-methoxypyridyl), 4-(2-nitroypyridyl), 4-(2-chloropyridyl) or 4-(3-hydroxypyridyl) radical.

When X is a $C_1$–$C_4$ alkylene radical or a vinylene radical and Py represents a 2-, 3- or 4-pyridyl radical, there are especially preferred in this sense 3-pyridylmethyl, 3-pyridylethyl, 3-pyridylvinyl, 4-pyridylmethyl, 4-pyridylethyl and 4-pyridylvinyl radicals.

Preferred pyrrolobenzimidazoles of general formula I are compounds in which $R_1$ signifies hydrogen, methyl, ethyl, 2-propyl, 2-methylpropyl or cyclopentyl, $R_2$ signifies hydrogen, methyl, ethyl, ethoxycarbonyl or hydrazinocarbonyl or $R_1$ and $R_2$, together with the carbon atom to which they are attached, form a cyclopentane ring or together represent an isopropylidene radical, X signifies a valency bond or a methylene, ethylene or vinylene radical, T signifies an oxygen or sulphur atom and Py signifies a pyridyl-N-oxide radical or a pyridyl radical which can be substituted one or more times by hydroxyl, methoxy, methyl or halogen.

Especially preferred are compounds of general formula I in which T is oxygen, X is a valency bond, $R_1$ is hydrogen or methyl, $R_2$ is methyl, ethyl or ethoxycarbonyl and Py is a pyridine-N-oxide radical or a pyridyl radical which can be substituted by hydroxyl or methyl.

The compounds of general formula I can be prepared in one of the following ways:

(a) o-cyanobenzyl nitrile of the formula:

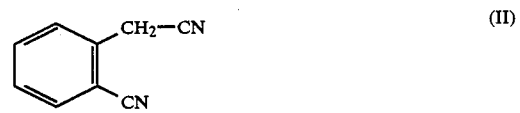
(II)

is alkylated with a compound of the general formula:

$$R_1 - Z \quad \text{(III)}$$

or with a compound of the general formula:

$$Z - R_3 - Z \quad \text{(IV)}$$

in which $R_1$ has the same meaning as above, $R_3$ is a $C_2$–$C_6$ alkylene group and Z is a group which can be split off, to give a compound of the general formula:

(V)

in which $R_1$ and $R_2$ have the same meanings as above, which is subsequently cyclised in an acidic medium to give a compound of the general formula:

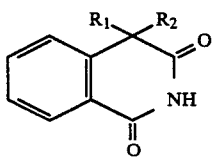
(VI)

in which $R_1$ and $R_2$ have the same meanings as above, or (b) isoquinoline-1,3-dione is alkylated with a compound of general formula III or IV to give a compound of the general formula VI, or (c) isoquinoline-1,3-dione is condensed with a compound of the general formula:

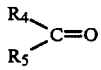
(VII)

in which $R_4$ and $R_5$ are hydrogen atoms and/or alkyl radicals or $R_4$ together with $R_5$ form a $C_3$-$C_7$ cycloalkylene radical, in the presence of a base to give a compound of the general formula:

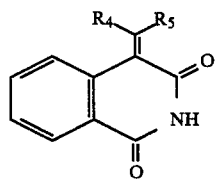
(VIII)

in which $R_4$ and $R_5$ have the same meanings as above, and possibly subsequently compounds of general formula VIII are converted by catalytic hydrogenation into compounds of general formula VI in which $R_1$ or $R_2$ is hydrogen.

A group Z which can be split off in general formulae III and IV is, as a rule, a halogen atom, chlorine, bromine and iodine thereby being preferred.

The cyclising of a compound of general formula V takes place in an acidic medium, preferably in the presence of a mineral acid, such as hydrochloric acid or sulphuric acid.

The condensation of isoquinoline-1,3-dione with a compound of general formula VII takes place in the presence of a base, preferably of potassium hydroxide or sodium hydroxide.

The catalytic hydrogenation of compounds of general formula VIII preferably takes place with Pd/C in an alcoholic medium.

Compounds of general formula VI, as well as the preceding process steps, carried out are described in Federal Republic of Germany Patent Application No. P 34 10 168.3.

The compounds so obtained of general formula VI are converted in known manner, by nitration in the 7-position, into compounds of the general formula:

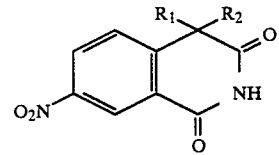
(IX)

in which $R_1$ and $R_2$ have the same meanings as above, from which, by Hoffmann reaction with hypohalide according to N. A. Joensson and P. Moses, Acta Chem. Scand., B28, 225-232/1974, there can be obtained compounds of the general formula:

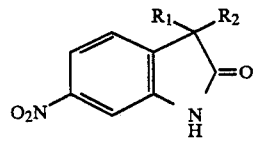
(X)

in which $R_1$ and $R_2$ have the same meanings as above.

By reduction of the nitro group to give an amino group, there are obtained compounds of the general formula:

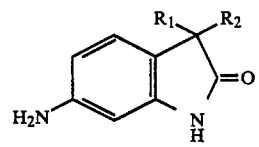
(XI)

in which $R_1$ and $R_2$ have the same meanings as above, which can also be obtained in known manner from appropriately substituted derivatives of 2,4-diaminophenylacetic acid by ring closure (see, in this regard R. C. Elderfield (ed.), P. L. Julian, E. W. Meyer, H. C. Printy, Heterocycl. Comp., Vol. 3, 126-186, pub. John Wiley & Sons, New York, 1952).

The so obtained compounds of general formula XI are converted in known manner, by acetylation of the amino group in the 6-position, nitration in the 5-position, splitting off of the protective group and reduction of the nitro group in the 5-position, into 5,6-diaminoindolin-2-ones of the general formula:

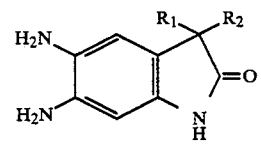
(XII)

in which $R_1$ and $R_2$ have the same meanings as above.

The preparation of compounds of general formula I can also take place in the following manner:

(d) compounds of general formula XII are obtained by alkylating an oxindole derivative, protected on the nitrogen atom, of the general formula:

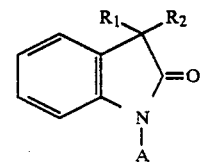
(XIII)

in which $R_1$ and $R_2$ are hydrogen atoms and A is a protective group, for example an acetyl or benzyl protective group, with compounds of general formulae III or IV with the above given meanings to give other compounds of general formula XIII in which $R_1$ and $R_2$ have the above-given meanings, except that $R_1$ and $R_2$ are not hydrogen atoms. After splitting off a benzyl protective group, for example by sodium in liquid ammonia, or of an acetyl protective group in an acidic or basic medium, there is obtained an indolin-2-one of general formula XIII in which A is a hydrogen atom and $R_1$ and $R_2$ have the above-given meanings, except that $R_1$ and $R_2$ are not hydrogen atoms.

The so obtained compounds of general formula XIII are converted in known manner, by nitration in the 5-position, subsequent reduction of the nitro group to an amino group, acetylation of the amino group in the 5-position, nitration in the 6-position, splitting off of the protective group and reduction of the nitro group in the 5-position, into corresponding 5,6-diaminoindolin-2-one derivatives of general formula XII with the above-given definitions.

The process according to the present invention for the preparation of compounds of general formula I takes place by reacting compounds of general formula XII with compounds of the general formula:

Py—X—CO—Y    (XIV)

in which Py and X have the above-given meanings and Y is either a hydrogen atom or a radical which can easily be split off, and the compounds obtained are cyclised to give compounds of general formula I or a tautomeric form thereof and compounds obtained according to the present invention of general formula I are, if desired, converted into other compounds of general formula I or tautomers thereof and/or compounds obtained of general formula I and the tautomers thereof are converted into physiologically acceptable acid addition salts with inorganic or organic acids.

By compounds of general formula XIV, there are to be understood, in particular, aldehydes, as well as acid halides, such as acid chlorides, carboxylic acid esters, such as methyl and ethyl esters, and other activated carboxylic acid derivatives, for example anhydrides.

If the compound of general formula XIV is an aldehyde, the reaction to give a Schiff's base takes place with a compound of general formula XII, preferably in an alcoholic medium, the subsequent cyclisation and oxidation to give a compound of general formula I taking place by warming the reaction mixture to reflux in the presence of atmospheric oxygen and a catalytic amount of an acid, for example toluence-sulphonic acid.

If the compound of general formula XIV is a carboxylic acid derivative, the reaction with a compound of general formula XII to give an amide takes place in an inert solvent, preferably in methylene chloride, and the subsequent cyclisation to give a compound of general formula I is carried out in an acidic medium, preferably in the presence of a mineral acid, for example sulphuric acid or hydrochloric acid, in an alcoholic solution.

Compounds of general formula I are also obtained
(e) by starting with compounds of the general formula:

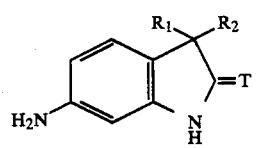

(XV)

or of the general formula:

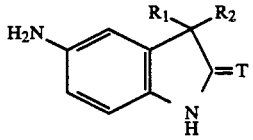

(XVI)

in which $R_1$, $R_2$ and T have the same meanings as above, by reacting with compounds of the general formula XIV, in which Y is a residue which can easily be split off, to give compounds of the general formula:

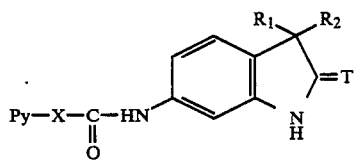

(XVII)

or compounds of the general formula:

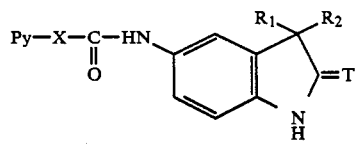

(XVIII)

in which $R_1$, $R_2$, T, Py and X have the same meanings as above, which are converted in known manner by nitration into compounds of the general formula:

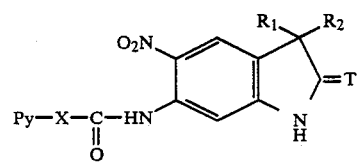

(XIX)

or of the general formula:

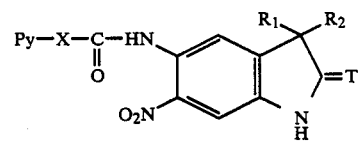

(XX)

in which $R_1$, $R_2$, T, Py and X have the same meanings as above.

After hydrogenation of the compounds of general formulae XIX and XX to give the corresponding amino compounds of the general formula:

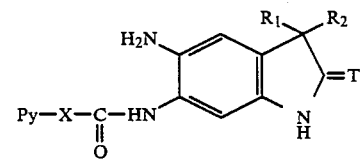

(XXI)

or of the general formula:

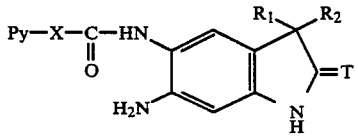 (XXII)

in which $R_1$, $R_2$, T, Py and X have the same meanings as above, there are obtained, by cyclisation, the desired compounds of general formula I.

Compounds of general formula XVI are obtained, for example, by nitration of compounds of the general formula:

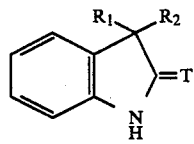 (XXIII)

in which $R_1$, $R_2$ and T have the same meanings as above, in the 5-position and subsequent reduction of the nitro group to an amino group.

The preparation of compounds of general formula I can also take place in the following manner:

(f) compounds of general formulae XV or XVI are acetylated on to 6- or 5-amino function in generally known manner and, by subsequent nitration and splitting off of the acetyl protective groups, there are obtained compounds of the general formula:

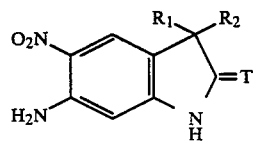 (XXIV)

or of the general formula:

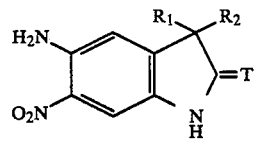 (XXV)

in which $R_1$, $R_2$ and T have the same meanings as above. By reaction with compounds of general formula XIV, there are also obtained, in the above-described manner, compounds of general formula XIX or XX.

(g) Compounds of general formula I or their tautomeric forms, as well as the intermediate products leading to them, can, apart from the above-described processes, also be prepared by various processes known from the literature, for example from compounds of the general formula:

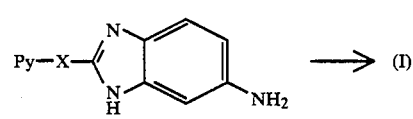 (XXVI)

in which Py and X have the above-given meanings (see, in this regard, R. C. Elderfield (ed.), P. L. Julian, E. W. Meyer, H. C. Printy, Heterocycl. Comp., Vol. 3, 126–186, 1952, pub. John Wiley & Sons, New York).

Thus, for example, a compound of general formula XXVI is acylated with a reactive derivative of a carboxylic acid of the general formula:

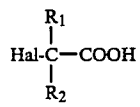 (XXVII)

preferably an acid chloride, and cyclised with a Lewis acid (aluminum chloride) (Stollésynthesis), in which Hal can be chlorine, bromine or iodine and $R_1$ and $R_2$ have the same meanings as above. The 7-monosubstituted compounds of general formula I can preferably be prepared by this method.

According to another variant, compounds of the general formula:

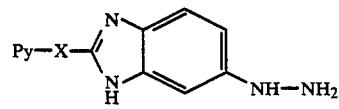 (XXVIII)

are reacted with a reactive derivative of a carboxylic acid of the general formula:

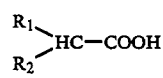 (XXIX)

preferably an acid chloride, in which $R_1$ and $R_2$ have the above-given meanings, to give corresponding hydrazides and these are then cyclised under alkaline conditions (Brunner synthesis).

Reactive carboxylic acid derivatives of general formulae XXVII and XXIX are especially acid chlorides, anhydrides and mesyl and tosyl esters.

Corresponding compounds of general formula I or the intermediate products leading thereto can also be obtained by reacting phenyl hydraine or appropriately substituted phenyl hydrazines in the manner described by K. Brunner (Monatsh. f. Chemie, 18, 95/1897) or, for example, by alkylating 2,4-dinitrochlorobenzene with appropriately substituted malonic acid derivatives, for example the sodium salt of methylmalonic acid diethyl ester, by processes known from the literature, subsequent reduction of the nitro groups and ring closure to give comnpounds of general formula XV.

The above-mentioned hydrogenation of a nitro group in the processes described under (a) to (g) to give compounds of general formula I is preferably carried out in a solvent or solvent mixture, for example water, ethanol, glacial acetic acid, ethyl acetate or dimethylformamide, with hydrogen in the presence of a catalyst, such as Raney nickel, platinum or palladium/charcoal, with metals, such as iron, tin or zinc, in the presence of an acid, with salts, such as ferrous sulphate, stannous chloride, sodium sulphide, sodium hydrogen sulphide or sodium dithionite, or with hydrazine in the presence of Raney nickel at a temperature of from 0° to 100° C. but preferably at ambient temperature.

The cyclisations mentioned above in processes (a) to (g) to give the desired compounds of general formula I are preferably carried out in a solvent or solvent mixture, for example ethanol, isopropanol, glacial acetic acid, benzene, toluene, chlorobenzene, glycol, ethylene glycol dimethyl ether, sulfolane or dimethylformamide, at a temperature of from 0° to 220° C. but preferably at the boiling temperature of the reaction mixture, optionally in the presence of a condensation agent, for example, phosphorus oxychloride, thionyl chloride, p-toluenesulphonic acid, hydrochloric acid, sulphuric acid, phosphoric acid or polyphosphoric acid, or possibly also in the presence of a base, for example, sodium hydroxide, sodium methylate or potassium tert.-butylate. However, the cyclisation can also be carried out without the use of solvents and/or of condensation agents.

The subsequent conversion of a compound of generally formula I into another compound of general formula I is concerned, for example, with the oxidation of the pyridyl radical into the corresponding N-oxide, which mainly takes place with hydrogen peroxide in acetic acid, as well as the hydrogenation of an unsaturated substituent. This applies especially to the hydrogenation of a vinyl compound (X=—CH=CH—) to give the corresponding ethyl compound.

The subsequent conversion of a compound of general formula I, in which $R_1$ and $R_2$ are hydrogen atoms, into another compound of general formula I is, for example, also concerned with the reaction of a compound of general formula VII with the above-given meaning in the presence of a base, such as ammonia or triethylamine, in alcoholic solution. In particular, this concerns the conversion of compounds of general formula I in which $R_1$ and $R_2$ are hydrogen atoms into compounds of general formula I in which $R_1$, together with $R_2$, represent an isopropylidene group, a cyclopentylidene group or a cyclohexylidene group, as well as possibly the hydrogenation thereof to give the corresponding compounds of general formula I in which $R_1$ or $R_2$ is hydrogen.

Furthermore, the subsequent conversion of compounds of general formula I in which $R_1$ or $R_2$ is a carboxyl group or a reactive derivative thereof, for example a carboxylic acid ester or acid chloride, is concerned with the reaction with hydrazine, ammonia, a primary or secondary amine or a reactive derivative thereof to give new compounds of general formula I, in which $R_1$ or $R_2$ is a carbonyl group substituted by an amino, alkylamino, dialkylamino or hydrazino group. The subsequent conversion also concerns compounds of general formula I in which $R_1$ or $R_2$ is an aminocarbonyl group to give those in which $R_1$ or $R_2$ is a cyano group, as well as the subsequent conversion of a cyano group into a carboxyl, aminocarbonyl or alkoxycarbonyl group. These conversions are all carried out by methods which are generally used and are known from the literature.

The subsequent conversion to compounds of general formula I and to intermediate products leading to compounds of general formula I in which T is a sulphur atom from those in which T is an oxygen atom is carried out by processes known from the literature with a reagent transmitting the sulphur atom, for example phosphorus pentasulphide or 2,4-bis-(4-methoxyphenyl)-2,4-dithioxo-1,3,2,4-dithiaphosphetane, in an appropriate solvent, for example tetrahydrofuran, dioxan, ethylene glycol dimethyl ether, benzene, toluene or pyridine, at a temperature of from 0° C. to the boiling temperature of the reaction mixture.

The compounds of general formula XII, XIX, XX, XXIV and XXV in which $R_1$ is a hydrogen atom or an alkyl, alkenyl or a cycloalkyl radical and $R_2$ is a hydrogen atom, an alkyl, alkenyl or cyano group, a carbonyl group substituted by a hydroxyl, alkyl, alkoxy, amino, alkylamino, dialkylamino or hydrazino group or forms a cycloalkylene group with $R_1$ and, so far as is relevant, X is a valency bond, a $C_1$-$C_4$ alkylene group or a vinyl radical, T is an oxygen or sulphur atom and Py is a 2-, 3- or 4-pyridyl radical which can possibly be substituted one or more times by alkyl, alkoxy, hydroxyl, cyano or nitro, as well as by halogen, are new an also the subject of the present invention.

Compounds according to the present invention of general formula XII are, apart from those mentioned in the Examples, also the following compounds:
  5,6-diamino-3-acetylindolin-2-one
  5,6-diamino-3-acetyl-3-methylindolin-2-one
  5,6-diamino-3-allylindolin-2-one
  5,6-diamino-3-cyano-3-methylindolin-2-one
  5,6-diamino-3-cyclohexylindolin-2-one
  5,6-diamino-3-cyclopentylindolin-2-one
  5,6-diamino-3,3-diallylindolin-2-one
  5,6-diamino-3-ethoxycarbonylindolin-2-one
  5,6-diamino-3-ethoxycarbonyl-3-ethylindolin-2-one
  5,6-diamino-3-ethoxycarbonyl-3-methylindolin-2-one
  5,6-diamino-3-ethylindolin-2-one
  5,6-diamino-3-methoxycarbonylindolin-2-one
  5,6-diamino-3-methoxycarbonyl-3-methylindolin-2-one
  5,6-diamono-3-methylindolin-2-one
  5,6-diamino-3-(3-pentyl)-indolin-2-one
  5,6-diamino-3-(2-propyl)-indolin-2-one
  5,40  ,6'-diamino-spiro[cyclohexane-1,3'-indolin]-2'-one.

Compounds according to the present invention of general formula XXV are, apart from those mentioned in the Examples, also the following compounds:
  5-amino-6-nitro-3-acetylindolin-2-one
  5-amino-6-nitro-3-actyl-3-methylindolin-2-one
  5-amino-6-nitro-3-allylindolin-2-one
  5-amino-6-nitro-3-cyano-3-methylindolin-2-one
  5-amino-6-nitro-3-cyclohexylindolin-2-one
  5-amino-6-nitro-3-cyclopentylindolin-2-one
  5-amino-6-nitro-3,3-diallylindolin-2-one
  5-amino-6-nitro-3-ethoxycarbonylindolin-2-one
  5-amino-6-nitro-3-ethoxycarbonyl-3-ethylindolin-2-one
  5-amino-6-nitro-3-ethoxycarbonyl-3-methylindolin-2-one
  5-amino-6-nitro-3-ethylindolin-2-one
  5-amino-6-nitro-3-methoxycarbonylindolin-2-one
  5-amino-6-nitro-3-methoxycarbonyl-3-methylindolin-2-one
  5-amino-6-nitro-3-methylindolin-2-one
  5-amino-6-nitro-3-(3-pentyl)-indolin-2-one
  5-amino-6-nitro-3-(2-propyl)-indolin-2-one
  5-amino-6-nitro-3-(2-methylpropyl)-indolin-2-one
  5'-amino-6'-nitrospiro[cyclohexane-1,3'-indolin]-2'-one
  5'-amino-6'-nitrospiro[cyclopentane-1,3'-indolin]-2'-one
  5-amino6-nitro-3,3-dimethylindolin-2-thione
  5-amino-6-nitro-3-ethylindolin-2-thione
  5-amino-6-nitro-3-methylindolin-2-thione.

Compounds according to the present invention of general formula XXIV are, apart from those mentioned in the Examples, also the following compounds:
  6-amino-5-nitroindolin-2-one
  6-amino-5-nitro-3-acetylindolin-2-one
  6-amino-5-nitro-3-acetyl-3-methylindolin-2-one
  6-amino-5-nitro-3-allylindolin-2-one 6-amino-5-nitro-3-cyano-3-methylindolin-2-one
6-amino-5-nitro-3-cyclohexylindolin-2-one
6-amino-5-nitro-3-cyclopentylindolin-2-one
6-amino-5-nitro-3,3-diallylindolin-2-one
6-amino-5-nitro-3-ethoxycarbonylindolin-2-one
6-amino-5-nitro-3-ethoxycarbonyl-3-ethylindolin-2-one
6-amino-5-nitro-3-ethoxycarbonyl-3-methylindolin-2-one
6-amino-5-nitro-3-ethylindolin-2-one
6-amino-5-nitro-3-methoxycarbonylindolin-2-one
6-amino-5-nitro-3-methoxycarbonyl-3-methylindolin-2-one
6-amino-5-nitro-3-methylindolin-2-one
6-amino-5-nitro-3-(3-pentyl)-indolin-2-one
6-amino-5-nitro-3-(2-propyl)-indolin-2-one
6'-amino-5'-nitrospiro[cyclohexane-1,3'-indolin]-2'-one
6-amino-5-nitro-3,3-dimethylindolin-2-thione
6-amino-5-nitro-3-ethylindolin-2-thione
6-amino-5-nitro-3-methylindolin-2-thione.

Compounds according to the present invention of general formula XIX are, apart from those mentioned in the Examples, also the following compounds:
5-nitro-6-(3-pyridinoylamino)-indolin-2-one
3-acetyl-5-nitro-6-(3-pyridinoylamino)-indolin-2-one
3-acetyl-5-nitro-6-(4-pyridinoylamino)-indolin-2-one
3-acetyl-3-methyl-5-nitro-6-(3-pyridinoylamino)-indolin-2-one
3-allyl-5-nitro-6-(3-pyridinoylamino)-indolin-2-one
3-allyl-5-nitro-6-(4-pyridinoylamino)-indolin-2-one
3-cyano-3-methyl-5-nitro-6-(3-pyridinoylamino)-indolin-2-one
3-cyano-3-methyl-5-nitro-6-(4-pyridinoylamino)-indolin-2-one
3-cyclohexyl-5-nitro-6-(3-pyridinoylamino)-indolin-2-one
3-cyclohexyl-5-nitro-6-(4-pyridinoylamino)-indolin-2-one
3-cyclopentyl-5-nitro-6-(3-pyridinoylamino)-indolin-2-one
3,3-diallyl-5-nitro-6-(3-pyridinoylamino)-indolin-2-one
3,3-diallyl-5-nitro-6-(4-pyridinoylamino)-indolin-2-one
3,3dimethyl-5-nitro-6-(2-pyridinoylamino)-indolin-2-one
3,3-dimethyl-5-nitro-6-[2-(5-n-butyl-pyridinoylamino)]-indolin-2-one
3,3-dimethyl-5-nitro-6-[3-(6-cyanopyridinoylamino)]-indolin-2-one
3,3-dimethyl-5-nitro-6-[3-(6-methyl-pyridinoylamino)]-indolin-2-one
3,3-dimethyl-5-nitro-6-[4-(2-methyl-pyridinoylamino)]-indolin-2-one
3,3-dimethyl-5-nitro-6-[4-(2-hydroxypyridinoylamino)]-indolin-2-one
3-ethoxycarbonyl-5-nitro-6-(3-pyridinoylamino)-indolin-2-one
3-ethoxycarbonyl-5-nitro-6-(4-pyridinoylamino)-indolin-2-one
3-ethoxycarbonyl-3-ethyl-5-nitro-6-(3-pyridinoylamino)-indolin-2-one
3-ethoxycarbonyl-3-ethyl-5-nitro-6-(4-pyridinoylamino)-indolin-2-one
3-ethoxycarbonyl-3-methyl-5-nitro-6-(3-pyridnoylamino)-indolin-2-one
3-methoxycarbonyl-5-nitro-6-(3-pyridinoylamino)-indolin-2-one
3-methoxycarbonyl-5-nitro-6-(4-pyridinoylamino)-indolin-2-one
3-methoxycarbonyl-3-methyl-5-nitro-6-(3-pyridinoylamino)-indolin-2-one
3-methoxycarbonyl-3-methyl-5-nitro-6-(4-pyridinoylamino)-indolin-2-one
3-(3-pentyl)-5-nitro-6-(3-pyridinoylamino)-indolin-2-one
3-(3-pentyl)-5-nitro-6-(4-pyridinoylamino)-indolin-2-one
3-(2-propyl)-5-nitro-6-(3-pyridinoylamino)-indolin-2-one
3-(2-methylpropyl)-5-nitro-6-(3-pyridinoylamino)-indolin-2-one
3-(2-methylpropyl)-5-nitro-6-(4-pyridinoylamino)-indolin-2-one
5'-nitro-6'-(3-pyridinoylamino)-spiro[cyclohexane-1,3'-indolin]-2'-one
5'-nitro-6'-(4-pyridinoylamino)-spiro[cyclohexane-1,3'-indolin]-2'-one
5'-nitro-6'-(3-pyridinoylamino)-spiro[cyclopentane-1,3'-indolin]-2'-one
5'-nitro-6'-(4-pyridinoylamino)-spiro[cyclopentane-1,3'-indolin]-2'-one
3,3-dimethyl-5-nitro-6-(2-pyridinoylamino)-indolin-2-thione
3,3-dimethyl-5-nitro-6-(3-pyridinoylamino)-indolin-2-thione
3,3-dimethyl-5-nitro-6-(4-pyridinoylamino)-indolin-2-thione
3-ethyl-5-nitro-6-(2-pyridinoylamino)-indolin-2-thione
3-ethyl-5-nitro-6-(3-pyridinoylamino)-indolin-2-thione
3-ethyl-5-nitro-6-(4-pyridinoylamino)-indolin-2-thione
3-methyl-5-nitro-6-(2-pyridinoylamino)-indolin-2-thione
3-methyl-5-nitro-6-(3-pyridinoylamino)-indolin-2-thione
3-methyl-5-nitro-6-(4-pyridinoylamino)-indolin-2-thione.

Compounds according to the present invention of general formula XX are, apart from those mentioned in the Examples, also the following compounds:
6-nitro-5-(3-pyridinoylamino)-indolin-2-one
6-nitro-5-(4-pyridinoylamino)-indolin-2-one
3-acetyl-6-nitro-5-(3-pyridinoylamino)-indolin-2-one
3-acetyl-6-nitro-5-(4-pyridinoylamino)-indolin-2-one
3-acetyl-3-methyl-6-nitro-5-(3-pyridinoylamino)-indolin-2-one
3-acetyl-3-methyl-6-nitro-5-(4-pyridinoylamino)-indolin-2-one
3-allyl-6-nitro-5-(3-pyridinoylamino)-indolin-2-one
3-allyl-6-nitro-5-(4-pyridinoylamino)-indolin-2-one
3-cyano-3-methyl-6-nitro-5-(3-pyridinoylamino)-indolin-2-one
3-cyano-3-methyl-6-nitro-5-(4-pyridinoylamino)-indolin-2-one
3-cyclohexyl-6-nitro-5-(3-pyridinoylamino)-indolin-2-one
3-cyclohexyl-6-nitro-5-(4-pyridinoylamino)-indolin-2-one
3-cyclopentyl-6-nitro-5-(3-pyridinoylamino)-indolin-2-one 3-cyclopentyl-6-nitro-5-(4-pyridinoylamino)-indolin-2-one
3,3-diallyl-6-nitro-5-(3-pyridinoylamino)-indolin-2-one
3,3-diallyl-6-nitro-5-(4-pyridinoylamino)-indolin-2-one
3,3-diethyl-6-nitro-5-(3-pyridinoylamino)-indolin-2-one
3,3-diethyl-6-nitro-5-(4-pyridinoylamino)-indolin-2-one
3,3-dimethyl-6-nitro-5-(2-pyridinoylamino)-indolin-2-one
3,3-dimethyl-6-nitro-5-(3-pyridinoylamino)-indolin-2-one
3,3-dimethyl-6-nitro-5-[2-(5-n-butyl-pyridinoylamino)]-indolin-2-one
3,3-dimethyl-6-nitro-5-[3-(6-cyanopyridinoylamino)]-indolin-2-one
3,3-dimethyl-6-nitro-5-[3-(6-methyl-pyridinoylamino)]-indolin-2-one
3,3-dimethyl-6-nitro-5-[4-(2-methyl-pyridinoylamino)]-indolin-2-one
3,3-dimethyl-6-nitro-5-[4-(2-hydrox-ypyridinoylamino)]-indolin-2-one
3-ethoxycarbonyl-6-nitro-5-(3-pyridinoylamino)-indolin-2-one
3-ethoxycarbonyl-6-nitro-5-(4-pyridinoylamino)-indolin-2-one
3-ethoxycarbonyl-3-ethyl-6-nitro-5-(3-pyridinoylamino)-indolin-2-one
3-ethoxycarbonyl-3-ethyl-6-nitro-5-(4-pyridinoylamino)-indolin-2-one
3-ethoxycarbonyl-3-methyl-6-nitro-5-(3-pyridinoylamino)-indolin-2-one
3-ethoxycarbonyl-3-methyl-6-nitro-5-(4-pyridinoylamino)-indolin-2-one
3-ethyl-6-nitro-5-(3-pyridinoylamino)-indolin-2-one
3-ethyl-6-nitro-5-(4-pyridinoylamino)-indolin-2-one
3-methoxycarbonyl-6-nitro-5-(3-pyridinoylamino)-indolin-2-one
3-methoxycarbonyl-6-nitro-5-(4-pyridinoylamino)-indolin-2-one
3-methoxycarbonyl-3-methyl-6-nitro-5-(3-pyridinoylamino)-indolin-2-one
3-methoxycarbonyl-3-methyl-6-nitro-5-(4-pyridinoylamino)-indolin-2-one
3-methyl-6-nitro-5-(3-pyridinoylamino)-indolin-2-one
3-methyl-6-nitro-5-(4-pyridinoylamino)-indolin-2-one
3-(3-pentyl)-6-nitro-5-(3-pyridinoylamino)-indolin-2-one
3-(3-pentyl)-6-nitro-5-(4-pyridinoylamino)-indolin-2-one
3-(2-propyl)-6-nitro-5-(3-pyridinoylamino)-indolin-2-one
3-(2-propyl)-6-nitro-5-(4-pyridinoylamino)-indolin-2-one
3-(2-methylpropyl)-6-nitro-5-(3-pyridinoylamino)-indolin-2-one
3-(2-methylpropyl)-6-nitro-5-(4-pyridinoylamino)-indolin-2-one
6'-nitro-5'-(3-pyridinoylamino)-spiro[cyclohexane-1,3'-indolin]-2'-one
6'-nitro-5'-(4-pyridinoylamino)-spiro[cyclohexane-1,3'-indolin]-2'-one
6'-nitro-5'-(3-pyridinoylamino)-spiro[cyclopentane-1,3'-indolin]-2'-one
6'-nitro-5'(4-pyridinoylamino)-spiro[cyclopentane-1,3'-indolin]-2'-one
3,3-dimethyl-6-nitro-5-(2-pyridinoylamino)-indolin-2-thione
3,3-dimethyl-6-nitro-5-(3-pyridinoylamino)-indolin-2-thione
3,3-dimethyl-6-nitro-5-(4-pyridinoylamino)-indolin-2-thione
3-ethyl-6-nitro-5-(2-pyridinoylamino)-indolin-2-thione
3-ethyl-6-nitro-5-(3-pyridinoylamino)-indolin-2-thione
3-ethyl-6-nitro-5-(4-pyridinoylamino)-indolin-2-thione
3-methyl -6-nitro-5-(2-pyridinoylamino)-indolin-2-thione
3-methyl -6-nitro-5-(3-pyridinoylamino)-indolin-2-thione
3-methyl -6-nitro-5-(4-pyridinoylamino)-indolin-2-thione.

For the conversion of compounds of general formula I or of their tautomeric forms into their pharmacologically acceptable salts, these are reacted, preferably in an organic solvent, with the equivalent amount of an inorganic or organic acid, for example hydrochloric acid, hydrobromic acid, phosphoric acid, sulphuric acid, acetic acid, citric acid, tartaric acid, maleic acid, fumaric acid, benzoic acid or cyclohexylsulphaminic acid.

For the preparation of medicaments, the compounds of general formula I are mixed in known manner with appropriate pharmaceutical carrier substances, aroma, flavouring and colouring materials and formed, for example, into tablets or dragees or, with the addition of appropriate adjuvants, are suspended or dissolved in water or an oil, for example olive oil.

The new compounds of general formula I according to the present invention and their salts can be administered enterally or parenterally in liquid or solid form. As injection medium, it is preferable to use water which contains the additives usual in the case of injection solutions, such as stabilising agents, solubilising agents or buffers.

Such additives are, for example, tartrate and citrate buffers, ethanol, complex formers (such as ethylenediamine-tetraacetic acid and the non-toxic salts thereof) and high molecular weight polymers (such as liquid polyethylene oxide) for viscosity regulation. Solid carrier materials are, for example, starch, lactose, mannitol, methyl cellulose, talc, highly dispersed silicic acids, high molecular weight fatty acids (such as stearic acid), gelatine, agar-agar calcium phosphate, magnesium stearate, animal and vegetable fats and solid high molecular weight polymers (such as polyethylene glycols). Compositions suitable for oral administration can, if desired, contain flavouring and sweetening agents.

The compounds of general formula I according to the present invention are usually administered in amounts of from 10 to 500 mg. per day, referred to a body weight of 75 kg. It is preferred to administer 2 to 3 times a day 1 to 2 tablets with an active material content of from 5 to 200 mg. The tablets can also be retarded, whereby 1 to 2 tablets containing 10 to 500 mg. of active material need be given only once per day. The active material can also be administered by injection 1 to 8 times per day or by continuous infusion, amounts of from 5 to 200 mg. per day normally being sufficient.

Preferred compounds according to the present invention are, apart from those mentioned in the Examples, also the following compounds and the tautomers thereof:

2-(3-pyridyl)-6,7-dihydro-3H,5H-pyrrolo[2,3-f]benzimidazol-6-one
7-acetyl-2-(3-pyridyl)-6,7-dihydro-3H,5H-pyrrolo[2,3-f]benzimidazol-6-one
7-acetyl-2-(4-pyridyl)-6,7-dihydro-3H,5H-pyrrolo[2,3-f]benzimidazol-6-one
7-acetyl-7-methyl-2-(3-pyridyl)-6,7-dihydro-3H,5H-pyrrolo[2,3-f]benzimidazol-6-one
7-acetyl-7-methyl-2-(4-pyridyl)-6,7-dihydro-3H,5H-pyrrolo[2,3-f]benzimidazol-6-one
7-allyl-2-(3-pyridyl)-6,7-dihydro-3H,5H-pyrrolo[2,3-f]benzimidazol-6-one
7-allyl-2-(4-pyridyl)-6,7-dihydro-3H,5H-pyrrolo[2,3-f]benzimidazol-6-one
7-aminocarbonyl-7methyl-2-(3-pyridyl)-6,7-dihydro-3H,5H-pyrrolo[2,3-f]benzimidazol-6-one
7-aminocarbonyl-7methyl-2-(4-pyridyl)-6,7-dihydro-3H,5H-pyrrolo[2,3-f]benzimidazol-6-one
7-cyano-7methyl-2-(3-pyridyl)-6,7-dihydro-3H,5H-pyrrolo[2,3-f]benzimidazol-6-one
7-cyano-7methyl-2-(4-pyridyl)-6,7-dihydro-3H,5H-pyrrolo[2,3-f]benzimidazol-6-one
7-cyclohexyl-2-(3-pyridyl)-6,7-dihydro-3H,5H-pyrrolo[2,3-f]benzimidazol-6-one
7-cyclohexyl-2-(4-pyridyl)-6,7-dihydro-3H,5H-pyrrolo[2,3-f]benzimidazol-6-one
7-cyclopentyl-2-(3-pyridyl)-6,7-dihydro-3H,5H-pyrrolo[2,3-f]benzimidazol-6-one
7,7-diallyl-2-(3-pyridyl)-6,7-dihydro-3H,5H-pyrrolo[2,3-f]benzimidazol-6-one
7,7-diallyl-2-(4-pyridyl)-6,7-dihydro-3H,5H-pyrrolo[2,3-f]benzimidazol-6-one
7,7-diethyl-2-(3-pyridyl)-6,7-dihydro-3H,5H-pyrrolo[2,3-f]benzimidazol-6-one
7,7-diethyl-2-(4-N-oxypyridyl)-6,7-dihydro-3H,5H-pyrrolo[2,3-f]benzimidazol-6-one
7,7-diethyl-2-(4-(2-methylpyridyl))-6,7-dihydro-3H,5H-pyrrolo[2,3-f]benzimidazol-6-one
7,7-diethyl-2-(4-pyridylethyl)-6,7-dihydro-3H,5H-pyrrolo[2,3-f]benzimidazol-6-one
7,7-dimethyl-2-(2N-oxypyridyl)-6,7-dihydro-3H,5-pyrrolo[2,3-f]benzimidazol-6-one
7,7-dimethyl-2-[2-(5-n-butylpyridyl)]-6,7-dihydro-3H,5H-pyrrolo[2,3-f]benzimidazol-6-one
7,7-dimethyl-2-[3-(6-cyanopyridyl)]-6,7-dihydro-3H,5H-pyrrolo[2,3,-f]benzimidazol-6-one
7,7-dimethyl-2-[3-(6-hydroxypyridyl)]-6,7-dihydro-3H,5H-pyrrolo[2,3,-f]benzimidazol-6-one
7,7-dimethyl-2-[3-(6-nitropyridyl)]-6,7-dihydro-3H,5H-pyrrolo[2,3,-f]benzimidazol-6-one
7,7-dimethyl-2-[4-(2-ethylpyridyl)]-6,7-dihydro-3H,5H-pyrrolo[2,3-f]benzimidazol-6-one
7,7-dimethyl-2-[4-(2-methoxypyridyl)]-6,7-dihydro-3H,5H-pyrrolo[2,3-f]benzimidazol-6-one
7,7-dimethyl-2-[4-(2-nitropyridyl)]-6,7-dihydro-3H,5H-pyrrolo[2,3-f]benzimidazol-6-one
7,7-dimethyl-2-(3-pyridylmethyl)-6,7-dihydro-3H,5H-pyrrolo[2,3-f]benzimidazol-6-one
7,7-dimethyl-2-(3-pyridylethyl)-6,7-dihydro-3H,5H-pyrrolo[2,3-f]benzimidazol-6-one
7,7-dimethyl-2-(4-pyridylvinyl)-6,7-dihydro-3H,5H-pyrrolo[2,3-f]benzimidazol-6-one
7-ethoxygarbonyl-2-(3-pyridyl)-6,7-dihydro-3H,5H-pyrrolo[2,3-f]benzimidazol-6-one
7-ethoxycarbonyl-2-(4-pyridyl)-6,7-dihydro-3H,5H-pyrrolo[2,3-f]benzimidazol-6-one
7-ethoxycarbonyl-7-ethyl-2-(3-pyridyl)-6,7-dihydro-3H,5H-pyrrolo[2,3-f]benzimidazol-6-one
7-ethoxycarbonyl-7-ethyl-2-(4-pyridyl)-6,7-dihydro-3H,5H-pyrrolo[2,3-f]benzimidazol-6-one
7-ethoxycarbonyl-7methyl-2-(3-pyridyl)6,7-dihydro-3H,5H-pyrrolo[2,3-f]benzimidazol-6-one
7ethyl-2-(3-N-oxypyridyl)-6,7-dihydro-3H,5H-pyrrolo-[2,3-f]benzimidazol-6-one
7ethyl-2-(4-N-oxypyridyl)-6,7-dihydro-3H,5H-pyrrolo-[2,3-f]benzimidazol-6-one
7-hydrazinocarbonyl-7methyl-2-(3-pyridyl)-6,7-dihydro-3H,5H-pyrrolo[2,3-f]benzimidazol-6-one
7-isopropylidene-2-(3-pyridyl)-6,7-dihydro-3H,5H-pyrrolo[2,3-f]benzimidazol-6-one
7-methoxycarbonyl-2-(3-pyridyl)-6,7-dihydro-3H,5H-pyrrolo[2,3-f]benzimidazol-6-one
7-methoxycarbonyl-2-(4-pyridyl)-6,7-dihydro-3H,5H-pyrrolo[2,3-f]benzimidazol-6-one
7-methoxycarbonyl-7methyl-2-(3-pyridyl)6,7-dihydro-3H,5H-pyrrolo[2,3-f]benzimidazol-6-one
7-methoxycarbonyl-7-methyl-2-(4-pyridyl-6,7-dihydro-3H,5H-pyrrolo[2,3-f]benzimidazol-6-one
7-methyl-2-(3-N-oxypyridyl)-6,7-dihydro-3H,5H-pyrrolo[2,3,-f]benzimidazol-6-one
7-(2-methylpropyl)-2-(3-pyridyl)-6,7-dihydro-3H,5-pyrrolo[b2,3-f]benzimidazol-6-one
7-(2-methylpropyl)-2-(4-pyridyl)-6,7-dihydro-3H,5H-pyrrolo[2,3-f]benzimidazol-6-one
7-(3-pentyl)-2-(3-pyridyl)-6,7-dihydro-3H,5H-pyrrolo[2,3-f]benzimidazol-6-one
7-(3-pentyl)-2-(4-pyridyl)-6,7-dihydro-3H,5H-pyrrolo[2,3-f]benzimidazol-6-one
7-(2-propyl)-2-(3-pyridyl)-6,7-dihydro-3H5H-pyrrolo[2,3-f]benzimidazol-6-one
7-(2-propyl)-2-[4-(2-methylpyridyl)]-6,7-dihydro-3H,5H-pyrrolo[2,3-f]benzimidazol-6-one
2'-(3-pyridyl)-spiro]cyclopropane-1,7'-6',7'-dihydro-3'H,5'H-pyrrolo[2',3'-f]benzimidazol]-6'-one
2'-(3-pyridyl)-spiro[cyclopentane-1,7'-6',7'-dihydro-3'H,5'H-pyrrolo[2',3'-f]benzimidazol]-6'-one
2'-(3-pyridyl)-spiro[cyclohexane-1,7'-6',7'-dihydro-3'H,5'H-pyrrolo[2',3'-f]benzimidazol]-6'-one
2'-(4-pyridyl)-spiro[cyclohexane-1,7'-6',7'-dihydro-3'H,5'H-pyrrolo[2',3'-f]benzimidazol]-6'-one
7,7-dimethyl-2-(2-pyridyl)-6,7-dihydro-3H,5H-pyrrolo[2,3-f]benzimidazol-6-thione
7,7-dimethyl-2-(3-pyridyl)-6,7-dihydro-3H,5H-pyrrolo[2,3-f]benzimidazol-6-thione
7,7-dimethyl-2-[3-(6-methylpyridyl)]-6,7-dihydro-3H,5H-pyrrolo[2,3-f]benzimidazol-6-thione
7,7-dimethyl-2-[4-(2-methylpyridyl)]-6,7-dihydro-3H,5H-pyrrolo[2,3-f]benzimidazol-6-thione
7-ethyl-2-(2-pyridyl)-6,7-dihydro-3H,5H-pyrrolo[2,3-f]benzimidazol-6-thione
7-ethyl-2-(3-pyridyl)-6,7-dihydro-3H,5H-pyrrolo[2,3-f]benzimidazol-6-thione
7-ethyl-2-(4-pyridyl)-6,7-dihydro-3H,5H-pyrrolo[2,3-f]benzimidazol-6-thione
7-methyl-2-(2-pyridyl)-6,7-dihydro-3H,5H-pyrrolo[2,3-f]benzimidazol-6-thione
7-methyl-2-(3-pyridyl)-6,7-dihydro-3H,5H-pyrrolo[2,3-f]benzimidazol-6-thione
7-methyl-2-(4-pyridyl)-6,7-dihydro-3H,5H-pyrrolo[2,3-f]benzimidazol-6-thione.

The following Examples are given for the purpose of illustrating the present invention:

EXAMPLE 1

7,7-Dimethyl-2-(4-pyridyl)-6,7-dihydro-3H,5H-pyrrolo[2,3-f]benzimidazol-6-one tetrahydrate 3 g. (0.017 mol) Isonicotinic acid chloride hydrochloride are added portionwise to a solution of 2.9 g. (0.015 mol) 5,6-diamino-3,3-dimethylindolin-2-one in 30 ml. methylene chloride containing 4.4 ml. (0.032 mol) triethylamine and the reaction mixture is left to stir overnight. It is then evaporated to dryness in a vacuum, the residue is stirred up several times with water, filtered off with suction and the crystals obtained are heated under reflux for about 12 hours in a solution of 100 ml. ethanol containing 10 ml. concentrated hydrochloric acid. The mixture obtained is evaporated to dryness in a vacuum, the residue is stirred up with 20 ml. water and then rendered neutral with an aqueous solution of ammonia. The product is subsequently filtered off with suction, washed with water, dried and recrystallised from water containing 30% ethanol. The yield is 1.9 g. (36% of theory); m.p. 215° C.

The following compounds are obtained in a manner analogous to that described in Example 1:

| designation | yield % | m.p. °C. solvent |
|---|---|---|
| (a) 7,7-dimethyl-2-(2-pyridyl)-6,7-dihydro-3H,5H-pyrrolo-[2,3-f]benzimidazol-6-one × 0.3 H$_2$O from 5,6-diamino-3,3-dimethyl-indolin-2-one and picolinic acid chloride | 79 | 182–187 water |
| (b) 7,7-dimethyl-2-(3-pyridyl)-6,7-dihydro-3H,5H-pyrrolo-[2,3-f]benzimidazol-6-one × 3 H$_2$O from 5,6-diamino-3,3-dimethyl-indolin-2-one and nicotinic acid chloride hydrochloride | 38 | 331–335 dioxan/ water (2:1 v/v) |
| (c) 7,7-dimethyl-2-(4-(2-methyl-pyridyl))-6,7-dihydro-3H,5H-pyrrolo[2,3-f]benzimidazol-6-one × 0.6 H$_2$O from 5,6-diamino-3,3-dimethyl-indolin-2-one and 2-methyl-isonicotinic acid chloride | 43 | 311–313 acetone |
| (d) 7,7-dimethyl-2-[4-(2-hydroxy-pyridyl)]-6,7-dihydro-3H,5H-pyrrolo[2,3-f]benzimidazol-6-one × 2 H$_2$O from 5,6-diamino-3,3-dimethyl-indolin-2-one and 2-hydroxy-isonicotinic acid chloride | 23 | >360 water |
| (e) 7,7-dimethyl-2-[4-(2-chloro-pyridyl)]-6,7-dihydro-3H,5H-pyrrolo]2,3-f]benzimidazol-6-one from 5,6-diamino-3,3-dimethyl-indolin-2-one and 2-chloro-isonicotinic acid chloride | 42 | 341–344 ethyl acetate |
| (f) 7,7-dimethyl-2-(3-pyridyl-vinyl)-6,7-dihydro-3H,5H-pyrrolo[2,3-f]benzimidazol-6-one × 0.75 H$_2$O from 5,6-diamino-3,3-dimethyl-indolin-2-one and 3-pyridyl-acrylic acid chloride hydrochloride | 17 | 203–207 water + 5% CH$_3$OH |
| (g) 7,7-dimethyl-2-(4-pyridyl-ethyl)-6,7-dihydro-3H,5H-pyrrolo[2,3-f]benzimidazol-6-one × 0.6 H$_2$O from 5,6-diamino-3,3-dimethyl-indolin-2-one and 4-pyridyl-propionic acid chloride hydrochloride | 35 | 150–154 water |
| (h) 2'-(4-pyridyl)-spiro[cyclo-pentan-1,7'-6',7'-dihydro-3'H,5'H-pyrrolo[2',3'-f]-benzimidazol]-6'-one × 0.3 H$_2$O from 5',6'-diamino-spiro[cyclo-pentan-1,3'-indolin]-2'-one and isonicotinic acid chloride hydrochloride | 48 | >365 ethanol |
| (i) 7,7-dimethyl-2-[3-(6-methyl-pyridyl)]-6,7-dihydro-3H,5H-pyrrolo[2,3-f]benzimidazol-6-one from 5,6-diamino-3,3-dimethyl-indolin-2-one and 6-methyl-nicotinic acid chloride | 52 | >360 ethyl acetate |

The starting materials for the compounds described in Example 1 can be prepared as follows:

4,4-Dimethyl-2H,4H-isoquinoline-1,3-dione (a) 142 g. (1mol) cyano-o-tolunitrile, together with 10.8 g. (0.03 mol) benzyltributylammonium bromide, are introduced into 700 ml. of concentrated aqueous sodium hydroxide solution and 185 ml. (2mol) methyl iodide added dropwise thereto, with ice cooling. The reaction mixture is stirred for 2 hours and the crystals obtained are filtered off with suction, washed with water and dried. There are obtained 170 g. (100% of theory) o-cyano-α,α-dimethylphenylacetic acid nitrile; m.p. 84°–88° C. The product obtained is introduced into 1500 ml. 90% sulphuric acid, stirred for 3 hours and the reaction mixture is poured on to ice. The crystallisate obtained is washed with water and dried. There are obtained 167 g. (88% of theory) of the title compound; m.p. 119°–120° C.

(b) 17.73 g. (0.32 mol) Potassium hydroxide are dissolved in 26.5 ml. water and 106 ml. ethanol and 25.55 g. (0.16 mol) 1,3-(2H,4H)isoquinolinedione are dissolved in this solution, with warming. After cooling the solution to ambient temperature, 45.44 g. (0.32 mol) methyl iodide are added dropwise thereto. After 1 hour at ambient temperature, stirring is continued for 1 hour at 80° C. The greater part of the ethanol is distilled off, the residue is mixed with 300 ml. hot water, cooled and the crystals obtained are filtered off with suction. The crystals are dissolved in a little 2N aqueous sodium hydroxide solution, precipitated out with a saturated aqueous solution of ammonium chloride and the product is filtered off with suction. By treatment with active charcoal and recrystallisation from ethanol, there are obtained 17 g. (57% of theory) of the pure product.

The following compound can be prepared in a manner analogous to that described in (a) or (b):

| designation | yield % | m.p. °C. solvent |
|---|---|---|
| spiro[cyclopentane-1,4'-2'H,4'H-isoquinoline]-1',3'-dione from cyano-o-tolunitrile and 1,4-dibromobutane | 90 | 136–138 ethanol |

(c) 4,4-Dimethyl-7-nitro-2H,4H-isoquinoline-1,3-dione

A solution of 46.2 ml. (1.1 mol) fuming nitric acid in concentrated sulphuric acid is added dropwise at 20° C. to a solution of 195 g. (1 mol) 4,4-dimethyl- 2H,4H-isoquinoline-1,3-dione in 1000 ml. concentrated sulphuric acid. The reaction mixture is stirred for one hour at ambient temperature and poured on to ice. The crystals obtained are filtered off with suction, well washed with water and dried and then recrystallised from ethanol. Yield: 206 g. (85% of theory); m.p. 211°–214° C.

The following compound can be prepared in a manner analogous to that described in (c):

| designation | yield % | m.p. °C. solvent |
|---|---|---|
| 7'-nitrospiro[cyclopentane-1,4'-2'H,4'H-isoquinoline]-1',3'-dione from spiro[cyclopentane-1,4'-2'H,4'H-isoquinoline]-1',3'-dione | 90 | 225–227 ethanol |

(d) 3,3-Dimethyl-6-nitroindolin-2-one.

54 ml. (1.05 mol) bromine are added dropwise at 0° C. to a solution of 210 g. (5.25 mol) sodium hydroxide in 1700 ml. water and subsequently 81.7 g. (0.35 mol) 4,4-dimethyl-7-nitro-2H,4H-isoquinoline-1,3-dione introduced. After stirring for 1 hour at ambient temperature, the reaction mixture is heated to 80° C. for 1 hour and, after cooling, acidified with acetic acid. The product obtained is filtered off with suction, well washed with water and dried. Yield: 49 g. (68% of theory); m.p. 241°–242° C.

The following compound can be synthesised in a manner analogous to that described in (d):

| designation | yield % | m.p. °C. solvent |
|---|---|---|
| 6'-nitrospiro[cyclopentane-1,3'-indolin]-2'-one from 7'-nitrospiro[cyclopentane-1,4'-2'H,4'H-isoquinoline]-1',3'-dione | 82 | 226–228 ethanol |

(e) 6-Amino-3,3-dimethylindolin-2-one.

A suspension of 146 g. (0.71 mol) 6-nitro-3,3-dimethylindolin-2-one in 3.5 liters methanol and 300 ml. glacial acetic acid are hydrogenated in the presence of 16 g. of 10%-Pd/C at 40° C., while being well stirred. The clear solution obtained is filtered off with suction from the catalyst and the filtrate is evaporated. Yield: 125 g. (100% of theory); m.p. 185°–190° C.

The following compound is obtained in a manner analogous to that described in (e):

| designation | yield % | m.p. °C. solvent |
|---|---|---|
| 6'-aminospiro[cyclopentane-1,3'-indolin]-2'-one from 6'-nitrospiro[cyclopentane-1,3'-indolin]-2'-one | 98 | 165–170 ethyl acetate |

(f) 6-Acetamido-3,3-dimethylindolin-2-one.

20.4 g (0.2 mol) Acetic anhydride are added dropwise, with cooling, to a suspension of 32 g. (0.18 mol) 6-amino-3,3-dimethyl-indolin-2-one in 500 ml. ethyl acetate and then stirred for about 1 hour at ambient temperature. The resultant product is filtered off with suction, well washed with ethyl acetate and dried. Yield: 37.8 g. (96% of theory); m.p. 275°–277° C.

The following compound is obtained in a manner analogous to that described in (f):

| designation | yield % | m.p. °C. solvent |
|---|---|---|
| 6'-acetamidospiro[cyclopentane-1,3'-indolin]-2'-one from 6'-aminospiro[cyclopentane-1,3'-indolin]-2'-one | 75 | 263–265 ethanol |

(g) 6-Acetamido-3,3-dimethyl-5-nitroindolin-2-one.

A solution of 7.6 ml. (0.18 mol) fuming nitric acid in 7.6 ml. concentrated sulphuric acid is added dropwise, with cooling, to a solution of 35 g. (0.16 mol) 6-acetamido-3,3-dimethylindolin-2-one in 200 ml. concentrated sulphuric acid. The reaction mixture is further stirred for 1 hour and poured on to ice. The crystals obtained are filtered off with suction, well washed with water and dried. Yield: 39 g. (92% of theory); m.p., 276°–280° C.

The following compound can be obtained in a manner analogous to that described in (g):

| designation | yield % | m.p. °C. solvent |
|---|---|---|
| 6'-acetamido-5'-nitrospiro-[cyclopentane-1,3'-indolin]-2'-one from 6'-acetamido-5'-nitrospiro-[cyclopentane-1,3'-indolin]-2'-one | 83 | 290–292 ethanol |

(h) 6-Amino-3,3-dimethyl-5-nitroindolin-2-one.

A solution of 36.2 g. (0.14 mol) 6-acetamido-3,3-dimethyl-5-nitroindolin-2-one in 180 ml. ethanol is heated under reflux for about 2 hours with 18 ml. concentrated aqueous sodium hydroxide solution, subsequently evaporated in a vacuum, adjusted to pH 6 and cooled in an ice-bath. The crystals obtained are filtered off with suction, washed with water and dried. Yield: 29.5 g. (97% of theory); m.p. 247°–248° C.

The following compound can be obtained in a manner analogous to that described in (h):

| designation | yield % | m.p. °C. solvent |
|---|---|---|
| 6'-amino-5'-nitrospiro[cyclopentane-1,3'-indolin]-2'-one from 6'-acetamido-5'-nitrospiro[cyclopentane-1,3'-indolin]-2'-one | 87 | 300–303 ethanol |

(i) 5,6-Diamino-3,3-dimethylindolin-2-one.

A solution of 18.7 g. (0.085 mol) 6-amino-3,3-dimethyl-5-nitroindolin-2-one in 200 ml. methanol is hydrogenated at 40° C. in the presence of 1.9 g. of 10% Pd/C. The catalyst is filtered off with suction, the filtrate is evaporated and the residue is crystallised from ethanol. Yield: 15.6 g. (96% of theory); m.p. 245°–247° C.

The following compound can be obtained in a manner analogous to that described in (i):

| designation | yield % | m.p. °C. solvent |
|---|---|---|
| 5',6'-diaminospiro[cyclopentane- | 100 | 255–256 |

-continued

| designation | yield % | m.p. °C. solvent |
|---|---|---|
| 1,3'-indolin]-2'-one from 6'-amino-5'-nitrospiro[cyclo-pentane-1,3'-indolin]-2'-one | | ethanol |

EXAMPLE 2

7,7-Dimethyl-2-(4-pyridylmethyl)-6,7-dihydro-3H,5H-pyrrolo[2,3-f]benzimidazol-6-one monohydrate

A suspension of 7.3 g. (0.038 mol) 5,6-diamino-3,3-dimethylindolin-2-one in 11.6 g. (0.077 mol) methyl 4-pyridylacetate is heated, while stirring, under an atmosphere of nitrogen for about 16 hours to 180° C. Subsequently, excess ester is distilled off in a vacuum and the residue obtained is separated on silica gel (elution agent: dichloromethane/ammonia-saturated methanol 20:1 v/v). Yield: 1.8 g. (16% of theory); m.p. 333°-337° C. (recrystallised from water/methanol 10:1 v/v).

EXAMPLE 3

7,7-Dimethyl-2-[3-(2-methoxy-6-methylpyridyl)]-6,7-dihydro-3H,5H-pyrrolo[2,3-f]benzimidazol-6-one

A solution of 3.8 g. (0.02 mol) 5,6-diamino-3,3-dimethylindolin-2-one with 3 g. (0.02 mol) 2-methoxy-6-methylpyridine-3-aldehyde and 0.4 g. (0.002 mol) toluenesulphonic acid in 50 ml. ethanol is heated under reflux for about 1 hour, whereby, after 30 minutes, air is introduced into the reaction mixture through an inlet tube. After cooling, precipitated substance is filtered off with suction and the filtrate is evaporated in a vacuum, the residue is stirred with water and then extracted with dichloromethane. The organic phase is evaporated and the residue is recrystallised from diethyl ether. The combined crude products are again recrystallised from ethyl acetate. Yield: 1.2 g. (19% of theory); m.p. 296°-298° C.

The following compounds are obtained analogously to Example 3:

| designation | yield % | m.p. °C. solvent |
|---|---|---|
| (a) 7,7-dimethyl-2-(2-pyridyl)-6,7-dihydro-3H,5H-pyrrolo-[2,3-f]benzimidazol-6-one × 0.3 H₂O from 5,6-diamino-3,3-dimethyl-indolin-2-one and pyridine-2-aldehyde | 25 | 182-187 water |
| (b) 7,7-dimethyl-2-(4-pyridyl)-6,7-dihydro-3H,5H-pyrrolo-[2,3-f]benzimidazol-6-one × 4 H₂O from 5,6-diamino-3,3-dimethyl-indolin-2-one and pyridine-4-aldehyde | 22 | 215 water/ ethanol |

EXAMPLE 4

7,7-Dimethyl-2-(4-N-oxypyridyl)-6,7-dihydro-3H,5H-pyrrolo[2,3-f]benzimidazol-6-one × 3H₂O.

A solution of 3.9 g. (0.014 mol) 7,7-dimethyl-2-(4-pyridyl)-6,7-dihydro-3H,5H-pyrrolo[2,3-f]benzimidazol-6-one in 50 ml. glacial acetic acid is stirred for 2 days at 50° C. with 20 ml. of 30% hydrogen peroxide and the reaction mixture then diluted with water. The precipitated substance is filtered off with suction and recrystallised from dioxan/water (1:1 v/v). Yield: 1.4 g. (34% of theory); m.p. 260°-262° C.

The following compounds are obtained analogously to Example 4:

| designation | yield % | m.p. °C. solvent |
|---|---|---|
| (a) 7,7-dimethyl-2-(3-N-oxy-pyridyl)-6,7-dihydro-3H,5H-pyrrolo[2,3-f]benzimidazol-6-one × 1.25 H₂O from 7,7-dimethyl-2-(3-pyridyl)-6,7-dihydro-3H,5H-pyrrolo-[2,3-f]benzimidazol-6-one | 12 | 355-358 water |
| (b) 7-methyl-2-(4-N-oxypyridyl)-6,7-dihydro-3H,5H-pyrrolo-[2,3-f]benzimidazol-6-one from 7-methyl-2-(4-pyridyl)-6,7-dihydro-3H,5H-pyrrolo[2,3-f]-benzimidazol-6-one | 11 | >300 ethyl acetate |

EXAMPLE 5

2-(4-Pyridyl)-6,7-dihydro-3H,5H-pyrrolo[2,3-f]-benzimidazol-6-one hydrochloride

0.2 g. (0.67 mmol) 6-Isonicotinoylamino-5-nitroindolin-2-one are suspended in 20 ml. glacial acetic acid, mixed with 80 mg. 10% Pd/charcoal and hydrogenated at normal pressure. After the hydrogenation, the catalyst is separated off by filtration, the filtrate is evaporated and the residue is dissolved in ethanol, filtered and acidified with ethanolic hydrochloric acid. After suction filtration and washing with ethanol, there is obtained 0.12 g. (62.5% of theory) of product; m.p. >300° C.; MS (trimethylsilyl derivative): M+ 394.466 m/z 73, 75, 379, 451.

The following compounds are obtained analogously to Example 5:

| designation | yield % | m.p. °C. solvent |
|---|---|---|
| (a) 7-methyl-2-(4-pyridyl)-6,7-dihydro-3H,5H-pyrrolo[2,3-f]-benzimidazol-6-one from 6-isonicotinoylamino-3-methyl-5-nitroindolin-2-one | 76 | 315-318 ethanol/ water |
| (b) 7-methyl-2-(3-pyridyl)-6,7-dihydro-3H,5H-pyrrolo[2,3-f]-benzimidazol-6-one from 3-methyl-6-nicotinoylamino-5-nitroindolin-2-one | 32 | >300 dioxan/ methanol |
| (c) 7-ethyl-2-(4-pyridyl)-6,7-dihydro-3H,5H-pyrrolo[2,3-f]-benzimidazol-6-one from 3-ethyl-6-isonicotinoylamino-5-nitroindolin-2-one | 36 | 270-272 ethyl acetate/ methanol |
| (d) 7-ethyl-2-(3-pyridyl)-6,7-dihydro-3H,5H-pyrrolo[2,3-f]-benzimidazol-6-one from 3-ethyl-6-nicotinoylamino-5-nitroindolin-2-one | 63 | >300 ethanol/ water |
| (e) 7-(2-propyl)-2-(4-pyridyl)-6,7-dihydro-3H,5H-pyrrolo-[2,3-f]benzimidazol-6-one from 6-isonicotinoylamino-3-(2-propyl)-5-nitroindolin-2-one | 66 | 215-220 ethanol/ water |
| (f) 7-cyclopentyl-2-(4-pyridyl)-6,7-dihydro-3H,5H-pyrrolo-[2,3-f]benzimidazol-6-one from 3-cyclopentyl-6-isonicotinoyl- | 75 | 200-204 dioxan/ methanol |

| designation | yield % | m.p. °C. solvent |
|---|---|---|
| amino-5-nitroindolin-2-one | | |

The starting materials for preparing the compounds described in Example 5 can be prepared as follows:

(a) 6-Isonicotinoylamino-5-nitroindolin-2-one 5.5 g. (21.7 mMol) 6-isonicotinoylaminoindolin-2-one are dissolved portionwise in 20 ml. concentrated sulphuric acid, cooled with ice and 2.19 g. (21.7 mMol) potassium nitrate dissolved in concentrated sulphuric acid slowly added dropwise thereto. After 2 hours, the solution is poured on to ice, neutralised and filtered with suction. The residue is substantially dissolved in 2N hydrochloric acid, filtered, treated with Floridin (fullers' earth), filtered with suction and neutralised. There are obtained 4.5 g. (70% of theory) of the title compound; m.p. >300° C.

The following compounds are obtained in an analogous manner:

| designation | yield % | m.p. °C. solvent |
|---|---|---|
| 6-isonicotinoylamino-3-methyl-5-nitroindolin-2-one sulphate from 6-isonicotinoylamino-3-methyl-indolin-2-one | 80 | >300 water |
| 3-methyl-6-nicotinoylamino-5-nitroindolin-2-one from 3-methyl-6-nicotinoylamino-indolin-2-one | 98 | 242–246 ethanol |
| 3-ethyl-6-isonicotinoylamino-5-nitroindolin-2-one from 3-ethyl-6-isonicotinoylamino-indolin-2-one | 70 | 232–235 ethanol |
| 3-ethyl-6-nicotinoylamino-5-nitroindolin-2-one from 3-ethyl-6-nicotinoylaminoindolin-2-one | 75 | 245–247 ethanol |
| 6-isonicotinoylamino-3-(2-propyl)-5-nitroindolin-2-one sulphate from 5-isonicotinoylamino-3-(2-propyl)-indolin-2-one | 83 | 294 water |
| 3-cyclopentyl-6-isonicotinoyl-amino-5-nitroindolin-2-one from 3-cyclopentyl-6-isonicotinoyl-amino-indolin-2-one | 85 | 186–190 methanol |

(b) Isonicotinoylaminoindolin-2-one 5.0 g. (27.1 mMol) 6-aminoindolin-2-one hydrochloride (Helv. Chim. Acta, 20, 373/1937) are suspended in 100 ml. methylene chloride, mixed with 3.7 ml. (27.1 mMol) triethylamine and stirred for 10 minutes. While cooling with ice, 6.73 g. (37.8 mMol) isonicotinic acid chloride hydrochloride and 5.24 ml. (37.8 mMol) triethylamine are added thereto. After 3 hours, the methylene chloride is distilled off and the residue is worked up with water and filtered with suction. The residue is stirred with hot ethanol. There are obtained 5.6 g. (82% of theory) of the title compound; m.p., 315°–320° C.

The following compounds are obtained in an analogous manner:

| designation | yield % | m.p. °C. solvent |
|---|---|---|
| 6-isonicotinoylamino-3-methyl-indolin-2-one from 6-amino-3-methylindolin-2-one hydrochloride | 74 | >300 ethanol |
| 3-methyl-6-nicotinoylamino-indolin-2-one from 6-amino-3-methylindolin-2-one hydrochloride | 88 | >300 ethanol |
| 3-ethyl-6-isonicotinoylamino-indolin-2-one from 6-amino-3-ethylindolin-2-one hydrochloride | 50 | 258–260 ethanol |
| 3-ethyl-6-nicotinoylamino-indolin-2-one from 6-amino-3-ethylindolin-2-one hydrochloride | 72 | 240–242 ethanol |
| 6-isonicotinoylamino-3-(2-propyl)-indolin-2-one from 6-amino-3-(2-propyl)-indolin-2-one | 65 | 223–225 ethanol |
| 3-cyclopentyl-6-isonicotinoyl-aminoindolin-2-one from 6-amino-3-cyclopentylindolin-2-one | 95 | 178–180 ethanol |

EXAMPLE 6

7,7-Diethyl-2-(4-pyridyl)-6,7-dihydro-3H,5H-pyrrolo-[2,3-f]benzimidazol-6-one×CH$_3$OH 5.4 g. (0.03 mol) isonicotinic acid chloride hydrochloride are added portionwise to a solution of 4.4 g. (0.02 mol) 5,6-diamino-3,3-diethylindolin-2-one in 100 ml. methylene chloride containing 8.4 ml. triethylamine. After about 2 hours, glacial acetic acid is added thereto and the crystals obtained are filtered off with suction, washed and dried. Subsequently, the crystals are heated under reflux for about 20 hours in a mixture of 100 ml. ethanol and 20 ml. concentration hydrochloric acid, then evaporated in a vacuum and the residue digested with a solution of ammonia, filtered off with suction and dried. The product is then purified on silica gel (elution agent: methylene chloride/ammonia-saturated methanol 15:1 v/v) and recrystallised from methanol. Yield: 2.4 g. (35% of theory); m.p. 216°–219° C.

The following compound is obtained in a manner analogous to that described in Example 6:

| designation | yield % | m.p. °C. solvent |
|---|---|---|
| 7,7-dimethyl-2-(4-pyridyl)-6,7-dihydro-3H,5H-pyrrolo[2,3-f]-benzimidazol-6-one tetrahydrate from 5,6-diamino-3,3-dimethylindolin-2-one and isonicotinic acid chloride hydrochloride | 41 | 215 ethanol/ water |

The starting materials for the compound described in Example 6 can be prepared as follows:

(a) 5,6-Diamino-3,3-diethylindolin-2-one

A solution of 10 g. (0.041 mol) 5-amino-3,3-diethyl-6-nitroindolin-2-one in 150 ml. ethanol is hydrogenated in the presence of 0.6 g. 10% Pd/C at ambient temperature. The catalyst is filtered off with suction, the filtrate is evaporated and the residue is recrystallised from ethanol. Yield: 8.5 g. (97% of theory); m.p. 167°–173° C.

The following compound can be prepared in a manner analogous to that described in (a):

| designation | yield % | m.p. °C. solvent |
|---|---|---|
| 5,6-diamino-3,3-dimethylindolin-2-one from 5-amino-3,3-dimethyl-6-nitro-indolin-2-one | 98 | 255–256 ethanol |

(b) 5-Amino-3,3-diethyl-6-nitroindolin-2-one

A solution of 72 g. (0.25 mol) 5-acetamido-3,3-diethyl-6-nitroindolin-2-one in 500 ml. ethanol is heated under reflux for about 3 hours with 100 ml. concentrated hydrochloric acid, then diluted with 1000 ml. water, filtered with suction and the crystals obtained are washed with aqueous ethanol and dried. Yield: 54.7 g. (89% of theory); m.p. 267°–272° C.

The following compound can be prepared in a manner analogous to that described in (b):

| designation | yield % | m.p. °C. solvent |
|---|---|---|
| 5-amino-3,3-dimethyl-6-nitro-indolin-2-one from 5-acetamido-3,3-dimethyl-6-nitroindolin-2-one | 82 | 247–250 ethanol/water |

(c) 5-Acetamido-3,3-diethyl-6-nitroindolin-2-one 24 ml. Fuming nitric acid are added dropwise to a solution of 84 g. (0.34 mol) 5-acetamido-3,3-diethylindolin-2-one in 800 ml. acetic anhydride, while cooling, and the reaction mixture further stirred for about 2 hours at ambient temperature. The reaction mixture is then carefully introduced into ice water and the crystals obtained are filtered off with suction, washed with water and dried. Yield: 72 g. (72% of theory); m.p. 182°–184° C.

The following compound can be prepared in a manner analogous to that described in (c):

| designation | yield % | m.p. °C. solvent |
|---|---|---|
| 5-acetamido-3,3-dimethyl-6-nitroindolin-2-one from 5-acetamido-3,3-dimethylindolin-2-one | 73 | 225–228 dichloromethane |

(d) 5-Acetamido-3,3-diethylindolin-2-one

A suspension of 86 g. (0.372 mol) 3,3-diethyl-5-nitroindolin-2-one in 700 ml. ethanol is hydrogenated in the presence of 4 g. 10% Pd/C., with good stirring. Subsequently, the clear solution is filtered off with suction and a sample recrystallised from ethanol (m.p. 188°–190° C.). The main amount of the solution is carefully mixed with 50 ml. acetic anhydride and evaporated in a vacuum. The residue is digested with ethyl acetate, filtered off with suction, washed and dried. The product is crystallised from ethyl acetate. Yield: 85 g. (94% of theory); m.p. 196°–197° C.

The following compound is obtained in a manner analogous to that described in (d):

| designation | yield % | m.p. °C. solvent |
|---|---|---|
| 5-acetamido-3,3-dimethylindolin-2-one from 5-nitro-3,3-dimethylindolin-2-one | 92 | 265–266 ethyl acetate |

(e) 3,3-Diethyl-5-nitroindolin-2-one

A solution of 17 ml. fuming nitric acid in 200 ml. of 80% sulphuric acid is added dropwise, while cooling, to a solution of 86 g. (0.462 mol) 3,3-diethylindolin-2-one in 500 ml. 80% sulphuric acid. The reaction mixture is stirred for about 30 minutes, then poured on to ice, filtered with suction, washed with water and dried. Yield: 86 g. (79% of theory); m.p. 174°–176° C.

The following compound can be obtained in a manner analogous to that described in (e):

| designation | yield % | m.p. °C. solvent |
|---|---|---|
| 3,3-dimethyl-5-nitroindolin-2-one from 3,3-dimethylindolin-2-one | 78 | ethanol |

EXAMPLE 7

7-Isopropylidene-2-(4-pyridyl)-6,7-dihydro-3H,5H-pyrrolo[2,3-f]benzimidazol-6-one Ammonia is passed up to saturation into a suspension of 0.4 g. (1.6 mmol) 2-(4-pyridyl)-6,7-dihydro-3H,5H-pyrrolo[2,3-f]benzimidazol-6-one in 20 ml. ethanol and 10 ml. acetone and the reaction mixture then stirred for 2 hours at 60° C. Subsequently, a further 10 ml. acetone are added thereto and stirring continued for 4 hours at 60° C., whereafter the reaction mixture is evaporated, the residue is taken up in ethanol, acidified and suction filtered from the precipitate. The residue obtained is dissolved in water and rendered neutral and the crystals obtained are filtered off with suction and recrystallised from isopropanol/ethyl acetate. Yield: 40 mg. (9% of theory); m.p. >300° C.

EXAMPLE 8

7-Ethoxycarbonyl-7-methyl-2-(4-pyridyl)-6,7-dihydro-3H,5H-pyrrolo[2,3-f]benzimidazol-6-one monohydrochloride A solution of 10.85 g. (32.2 mmol) 5-amino-3-ethoxycarbonyl3-methyl-6-(4-pyridinoylamino)-indolin-2-one in 700 ml. ethanol is heated under reflux for about 12 hours with 50 ml. concentrated hydrochloric acid. Subsequently, the reaction mixture is cooled, concentration somewhat and the crystals obtained are filtered off with suction and recrystallised from ethanol. Yield: 9.6 g. (79% of theory); m.p. 288°–290° C.

The starting materials for the compound described in Example 8 can be prepared as follows:

(a)
5-Amino-3-ethoxycarbonyl-3-methyl-6-(4-pyridinoylamino)-indolin-2-one

A solution of 12.4 g. (32.2 mmol) 3-ethoxycarbonyl-3-methyl-5-nitro-6-(4-pyridinoylamino)-indolin -2-one in 500 ml. methanol is hydrogenated at ambient temperature in the presence of 1 g. 10% Pd/C. The catalyst is filtered off with suction, the filtrate is evaporated and the substance obtained is immediately further worked up.

(b)
3-Ethoxycarbonyl-3-methyl-5-nitro-6-(4-pyridinoylamino)-indolin-2-one

A solution of 3.9 g. (0.038 mol) potassium nitrate in 30 ml. concentrated sulphuric acid is added dropwise, while cooling, to a solution of 13 g. (0.038 mol) 3-ethoxycarbonyl-3-methyl-6-(4-pyridinoylamino)-indolin-2-one in 90 ml. concentrated sulphuric acid. The reaction mixture is further stirred for about 1 hour, poured on to ice, adjusted to pH 8 with a concentrated aqueous solution of ammonia, while cooling, and the crystals obtained are filtered off with suction and recrystallised from ethanol/methylen chloride. Yield: 12.81 g. (82% of theory); m.p. 217°–219° C.

(c)
3-Ethoxycarbonyl-3-methyl-6-(4-pyridinoylamino)-indolin-2-one 22.1 ml. Triethylamine and 9.4 g. (0.053 mol) pyridine-4-carboxylic acid chloride hydrochloride are added to a cooled solution of 13 g. (0.048 mol) 6-amino-3-ethoxycarbonyl-3-methylindolin-2-one in 500 ml. methylene chloride and the reaction mixture then stirred at ambient temperature for about 2 hours. Subsequently, the reaction mixture is evaporated to dryness and the residue is stirred with water, filtered with suction and the product obtained is recrystallised from ethanol/methylene chloride. Yield: 11.0 g. (73% of theory); m.p. 222°–224° C.

(d) 6-Amino-3-ethoxycarbonyl-3-methylindolin-2-one

A solution of 27 g. (0.079 mol) methyl-2,4-dinitrophenyl)-malonic acid diethyl ester in 800 ml. ethanol is hydrogenated at ambient temperature in the presence of 1 g. 10% Pd/C. Subsequently, the catalyst is filtered off with suction and the filtrate is acidified with ethanolic hydrogen chloride solution, evaporated to dryness and the residue is crystallised out by the addition of isopropanol. Yield: 13.19 g. (71% of theory); m.p. 248° C.

EXAMPLE 9

7-Hydrazinocarbonyl-7-methyl-2-(4-pyridyl)-6,7-dihydro-3H,5H-pyrrolo[2,3-f]benzimidazol-6-one A solution of 1 g. (2.7·mol) 7-ethoxycarbonyl-7-methyl-2-(4-pyridyl)-6,7-dihydro-3H,5H-pyrrolo[2,3-f]bemzimidazol-6-one hydrochloride in 30 ml. ethanol is stirred at 80° C. for about 8 hours with 6 ml. hydrazine hydrate. Subsequently, the reaction mixture is filtered with suction, the product obtained is boiled up with a solution of 1000 ml. methanol and 500 ml. methylene chloride, concentrated somewhat and the crystals obtained are filtered off with suction, washed with methanol and dried. Yield: 0.6 g. (70% of theory); m.p.>300° C.

EXAMPLE 10

7,7-Dimethyl-2-(4-pyridyl)-6,7-dihydro-3H,5H-pyrrolo[2,3-f]benzimidazol-6-one tetrahydrate A solution of 68 g. (0.209 mol) 3,3-dimethyl-5-nitro-6-(4-pyridinoylamino)-indolin-2-one in 3000 ml. ethanol containing 30 ml. triethylamine is hydrogenated in the presence of 10% Pd/C. The catalyst is subsequently filtered off with suction, the filtrate is evaporated and the crude product obtained is heated under reflux for about 6 hours in 1000 ml. ethanol containing 200 ml. concentrated hydrochloric acid, thereafter concentrated, diluted with water and adjusted to pH 8 with an aqueous solution of ammonia. The crystallisate thus obtained is filtered off with suction, washed and crystallised from ethanol/water, Yield: 52.3 g. (71% of theory); m.p. 215° C.

The following compound is obtained in a manner analogous to that described in Example 10:

| designation | Yield % | m.p. °C. solvent |
|---|---|---|
| 7,7-dimethyl-2-(3-pyridyl)-6,7-dihydro-3H,5H-pyrrolo[2,3-f]-benzimidazol-6-one trihydrate from 3,3-dimethyl-5-nitro-6-(3-pyridinoylamino)-indolin-2-one | 45 | 331–335 dioxan water |

The starting materials used in Example 10 are prepared as follows:

(a)
3,3-Dimethyl-5-nitro-6-(4-pyridinoylamino)-indolin-2-one

A solution of 48.3 g. (0.22 mol) 6-amino-3,3-dimethyl-5-nitroindolin-2-one in 400 ml. pyridine is mixed portionwise with 78.8 g. (0.44 mol) isonicotinic acid chloride hydrochloride and then stirred for about 2 hours. Subsequently, the reaction mixture is poured on to water, rendered neutral, filtered with suction and the product obtained is recrystallised from ethanol. Yield: 68.1 g. (95% of theory); m.p. 225°–230° C.

The following compound is obtained in a manner analogous to that described in (a):

| designation | yield % | m.p. °C. solvent |
|---|---|---|
| 3,3-dimethyl-5-nitro-6-(3-pyridinoylamino)-indolin-2-one from 6-amino-3,3-dimethyl-5-nitro-indolin-2-one and nicotinic acid chloride hydrochloride | 95 | 225–230 ethanol |

EXAMPLE 11

7-(2-Methylpropyl)-2-(4-pyridyl)-6,7-dihydro-3H,5H-pyrrolo[2,3-f]benzimidazol-6-one sesquihydrate 1.6 g. (0.009 mol) isonicotinic acid chloride hydrochloride is added portionwise to a solution of 1.3 g. (0.006 mol) 5,6-diamino-3-(2-methylpropyl)-indolin-2-one in 40 ml. methylene chloride containing 3 ml. triethylamine. After about 2 hours, the reaction mixture is extracted with water and the organic phase is evaporated. The solid residue is heated under reflux overnight in 70 ml. ethanol containing 10 ml. concentrated hydrochloride acid, then evaporated, stirred up with an aqueous solution of ammonia and extracted with methylene chloride/methanol. The organic phase is evaporated and the residue is purified on silica gel (elution agent: methylene chloride/ammonia-saturated methanol 9:1 v/v).Yield: 0.65 g. (35% of theory); m.p. 200°–202° C.

The starting materials for Example 11 are obtained in the following manner:

(a) 5,6-Diamino-3-(2-methylpropyl)-indolin-2-one

A solution of 1.5 g. (0.006 mol) 6-amino-3-(2-methylpropyl)-5-nitroinsolin-2-one in 50 ml. methanol is hydrogenated in the presence of 0.3 g. 10% Pd/C. The catalyst is filtered off with suction, the filtrate is evaporated and the residue is recrystallised from ethanol. Yield: 1.3 g. (99% of theory).

(b) 6-Amino-3-(2-methylpropyl)-5-nitroindolin-2-one

A solution of 2.9 g. (0.01 mol) 6-acetamido-3-(2-methylpropyl)-5-nitroindolin-2-one in 50 ml. ethanol is heated under reflux for about 30 minutes with 3 ml. concentrated hydrochloric acid, evaporated and the residue purified on silica gel (elution agent: methylene chloride/ammonia-saturated methanol 20:1 v/v). Yield 1.5 g. (60% of theory).

(c) 6-Acetamido-3(2-methylpropyl)-5-nitroindolin-2-one

A solution of 4.2 g. (0.017 mol) 6-acetamido-3-(2-methylpropyl)-indolin-2-one in 50 ml acetic anhydride is mixed, while cooling, with 0.8 ml. (0.019 mol) fuming nitric acid and then stirred for about 30 minutes. Subsequently, the reaction mixture is carefully poured on to ice and the crystals obtained are filtered off with suction, washed with water and dried. Yield: 3.2 g. (66% of theory): m.p. 192°–197° C.

(d) 6-Aetamido-3-(2-methylpropyl)-indolin-2-one

A solution of 6.4 g. (0.026 mol) 6-acetamido-3-isopropylideneindolin-2-one in 100 ml. methanol is hydrogenated in the presence of 0.6 g. 10% Pd/C. Subsequently, the catalyst is filtered off with suction and the filtrate is evaporated to dryness. Yield: 5.5 g. (84% of theory); m.p. 214°–216° C.

(e) 6-Acetamido-3-isopropylideneindolin-2-one

A solution of 1.9 g. sodium hydroxide in 2 ml. water is added dropwise to a suspension of 9 g. (0.047 mol) 6-acetamidoindolin-2-one in 50 ml. ethanol containing 3.4 g. (0.047 mol) isobutyraldehyde. After about 5 hours, the reaction mixture is evaporated to dryness and the residue is purified on silica gel (elution agent: methylene chloride/ammonia-saturated methanol). Yield: 7.6 g. (65% of theory) of foam; m.p. 93° C.

EXAMPLE 12

7,7-Dimethyl-2-(4-pyridyl)-6,7-dihydro-3H,5H-pyrrolo[2,3-f]benzimidazol-6-thione dihydrate A solution of 2.0 g. (7.2 mmol) 7,7-dimethyl-2-(4-pyridyl)-6,7-dihydro-3H,5H-pyrrolo[2,3-f]benzimidazol-6-one imidazol-6-one in 35 ml. pyridine is heated for about 5 hours to 100° C. with 4 g. phosphorus pentasulphide (P$_4$S$_{10}$). Subsequently, the reaction mixture is decomposed with water, rendered alkaline and the desired product is extracted and purified on silica gel (elution agent: methylene chloride/ammonia-saturated methanol 20:1 v/v). Yield: 1.7 g. (72% of theory); m.p. 205°–220° C.

EXAMPLE 13

7,7-Dimethyl-2-(4-(3-hydroxypyridyl))-6,7dihydro-3H,5H-pyrrolo[2,3-f]benzimidazol-6-one A solution of 5.2 g (0.025 mol) dicyclohexylcarbodiimide in 20 ml. dimethylformamide is added at 0° C., with stirring, to a mixture of 2.8 g. (0.02 mol) 3-hydroxypyridine-4-carboxylic acid in 30 ml. dimethylformamide with 3 g. anhydrous calcium sulphate and 3.4 g. (0.025 mol) hydroxybenzotriazole. Subsequently, the reaction mixture is mixed with 2.8 g. (0.015 mol) 5,6-diamino-3,3-dimethylindolin-2-one and, after a short subsequent stirring, digested with water and filtered off with suction. The residue is heated under reflux with 200 ml. ethanol and 40 ml. concentrated hydrochloric acid for 2 days, cooled, filtered off with suction and the filtrate evaporated in a vacuum, digested with an aqueous solution of ammonia and filtered with suction. The product is purified by column chromatography on silica gel (elution agent: methylene chloride/methanol/acetic acid 10:1:1 v/v/v). Yield: 1.4 g. (24% of theory); m.p. >300° C.

The following compound is obtained in a manner analogous to that described in Example 13:

| designation | yield % | m.p. °C. solvent |
|---|---|---|
| 7,7-dimethyl-2-(4-(2-hydroxy-pyridyl))-6,7-dihydro-3H,5H-pyrrolo[2,3-f]benzimidazol-6-one dihydrate from 5,6-diamino-3,3-dimethylindolin-2-one and 2-hydroxypyridine-4-carboxylic acid | 22 | >360 water |

EXAMPLE 14

7,7-Dimethyl-2-(4-pyridyl)-6,7-dihydro-3H,5H-pyrrolo[2,3-f]benzimidazol-6-one 33 g. (0.1 mol) 3,3-dimethyl-6-nitro-5-(4-pyridinoylamino)-indolin-2-one in 1300 ml. ethanol containing 13 ml. triethylamine is hydrogenated in the presence of 10% Pd/C. Subsequently, the catalyst is filtered off with suction, the filtrate is evaporated and the residue is heated under reflux for about 6 hours in 500 ml. ethanol containing 100 ml. concentrated hydrochloric acid. The reaction mixture is then evaporated, digested with an aqueous solution of ammonia and the resultant product is filtered off with suction, washed with water crystallised from ethanol/water and recrystallised from methanol. Yield: 19.5 g. (70% of theory); m.p. 285°–288° C.

The starting compounds are prepared in the following manner:

(a) 3,3-Dimethyl-6-nitro-5-(4-pyridinoylamino)-indolin-2-one 2.5 ml. Fuming nitric acid are added, with cooling, to a solution of 5.5 g. (0.02 mol) 3,3-dimethyl-5-(5-pyridinoylamino)-indolin-2-one in 50 ml. glacial acetic acid and the reaction mixture then stirred at ambient temperature for about 2 hours. It is then carefully poured on to ice, neutralised and the crystals obtained are filtered off with suction, washed with water and dried. Yield: 5.2 g. (81% of theory); m.p. 310°–318° C. (from methanol).

(b) 3,3-Dimethyl-5-(4-pyridinoylamino)-indolin-2-one

A suspension of 5.0 g. (0.028 mol) 5-amino-3,3-dimethylindolin-2-one in 100 ml. methylene chloride containing 14 ml. triethylamine is mixed, while cooling, with 7.0 g. (0.04 mol) isonicotinic acid chloride hydrochloride. Subsequently, the reaction mixture is evaporated and the residue is digested with water, filtered with suction and recrystallised from ethanol. Yield: 5.8 g. (73% of theory); m.p.>300° C.

(c) 5-Amino-3,3-dimethylindolin-2-one

A suspension of 100 g. (0.48 mol) 5-nitroindolin-2-one in 2500 ml. methanol with 200 ml. glacial acetic acid is hydrogenated, while stirring well, at 40° C. in the presence of 10 g. of 10% Pd/C. The subsequently clear solution is freed from catalyst by suction filtration and the filtrate is evaporated. Yield: 82 g. (96% of theory); m.p. 185°–191° C. (HCl-salt from methanol).

(d) 3,3-Dimethyl-5-nitroindolin-2-one

A solution of 22 ml. fuming nitric acid in 200 ml. 80% sulphuric acid is added dropwise, with cooling, to a solution of 100 g. (0.62 mol) 3,3-dimethylindolin-2-one in 500 ml. 80% sulphuric acid. The reaction mixture is then stirred for about 30 minutes, poured on to ice, filtered with suction, washed with water and dried. Yield: 100 g. (78% of theory); m.p. 192°–196° C. (ethyl acetate/heptane).

EXAMPLE 15

7,7-Dimethyl-2-(4-pyridyl)-6,7-dihydro-3H,5H-pyrrolo[2,3-f]benzimidazol-6-one tetrahydrate 8 g. (0.04 mol) isonicotinic acid chloride hydrochloride is added portionwise to a solution of 5 g. (0.023 mol) 5-amino-3,3-dimethyl-6-nitroindolin-2-one in 50 ml. pyridine and the reaction mixture then stirred for about 2 hours. Subsequently, it is poured into water, digested with an aqueous solution of ammonia, filtered off with suction, washed with water and the residue is hydrogenated in 300 ml. ethanol containing 3 ml. triethylamine in the presence of 10% Pd/C. The catalyst is filtered off with suction, the filtrate is evaporated and the crude product obtained is heated under reflux for 6 hours in 100 ml. ethanol and 20 ml. concentrated hydrochloric acid, evaporated, rendered neutral and the product obtained is filtered off with suction, washed and crystallised from ethanol/water. Yield: 5.5 g. (69% of theory); m.p. 215° C.

The following compounds are obtained in a manner analogous to that described in Example 15:

| designation | yield % | m.p. °C. solvent |
|---|---|---|
| (a) 7,7-dimethyl-2-(2-pyridyl)-6,7-dihydro-3H,5H-pyrrolo-[2,3-f]benzimidazol-6-one x 0.3 H₂O from 5-amino-3,3-dimethyl-6-nitro-indolin-2-one and picolinic acid chloride | 60 | 182–187 water |
| (b) 7,7-dimethyl-2-(3-pyridyl)-6,7-dihydro-3H,5H-pyrrolo-[2,3-f]benzimidazol-6-one x 3 H₂O from 5-amino-3,3-dimethyl-6-nitro-indolin-2-one and nicotinic acid chloride hydrochloride | 55 | 331–335 dioxan/water |
| (c) 7,7-diethyl-2-(4-pyridyl)-6,7-dihydro-3H,5H-pyrrolo-[2,3-f]benzimidazol-6-one x CH₃OH from 5-amino-3,3-diethyl-6-nitro-indolin-2-one and isonicotinic acid chloride hydrochloride | 59 | 216–219 methanol |

EXAMPLE 16

7,7-Dimethyl-2-(4-pyridyl)-6,7-dihydro-3H,5H-pyrrolo[2,3-f]benzimidazol-6-one tetrahydrate 0.15 ml. Phosphorus oxychloride are added to a solution of 221 mg. (1 mmol) 6-amino-5-nitro-3,3-dimethyl-indolin-2-one in 2 ml. dimethylformamide containing 0.5 ml. pyridine and 123 mg. (4 mmol) isonicotinic acid. The reaction mixture is then stirred for about 3 hours, poured on to ice water and the crystals obtained are filtered off with suction. Subsequently, the product is hydrogenated in 10 ml. ethanol containing 0.2 ml. triethylamine in the presence of Pd/C. The catalyst is then filtered off with suction, the filtrate is evaporated and the residue is heated under reflux for about 6 hours in a solution of 5 ml. ethanol and 1 ml. concentrated hydrochloric acid. The reaction mixture is then evaporated, digested with an aqueous solution of ammonia and the product obtained recrystallised from ethanol/water. Yield: 220 mg. (63% of theory); m.p. 215° C.

The following compounds are obtained in a manner analogous to that described in Example 16:

| designation | yield % | m.p. °C. solvent |
|---|---|---|
| (a) 7,7-diethyl-2-(4-pyridyl)-6,7-dihydro-3H,5H-pyrrolo-]2,3-f]benzimidazol-6-one x CH₃OH from 5-amino-6-nitro-3,3-diethyl-indolin-2-one and isonicotinic acid | 62 | 216–219 methanol |
| (b) 7,7-dimethyl-2-(3-(6-methyl-pyridyl))-6,7-dihydro-3H,5H-pyrrolo[2,3-f]benzimidazol-6-one from 6-amino-5-nitro-3,3-dimethyl-indolin-2-one and 6-methyl-nicotinic acid | 55 | >360 ethyl acetate |
| (c) 7,7-dimethyl-2-(4-(2-methyl-pyridyl))-6,7-dihydro-3H,5H-pyrrolo[2,3-f]benzimidazol-6-one x 0.6 H₂O from 6-amino-5-nitro-3,3-dimethyl-indolin-2-one and 2-methyl-isonicotinic acid | 45 | 311–313 acetone |
| (d) 7,7-dimethyl-2-(4-pyridyl-ethyl)-6,7-dihydro-3H,5H-pyrrolo[2,3-f]benzimidazol-6-one x 0.6 H₂O from 6-amino-5-nitro-3,3-dimethyl-indolin-2-one and 4-pyridyl-propionic acid | 43 | 150–154 water |

PHARMACEUTICAL ACTIVITY

Examination method

Male Sprague-Dawley rats weighing between 350 and 450 g were narcotized by intraperitoneal injection of a barbiturate and fitted with instrumentation for the examinations as follows:

A pressure measuring catheter (Millar Mikrotip/diameter 0.5 mm) was inserted through the arteria carotis dextra into the left ventricle. The pressure inside the left ventricle was continually registered through this catheter. The signal from this Mikrotip was electronically differentiated and $(dp/dt)_{60}$—the slope of the pressure-time curve at a pressure of 60 mmHg—was taken as a measure for the inotropy.

A polypropylene catheter was bound in a vena jugularis for the intravenous injection of the test substances.

A further polypropylene catheter was inserted through an arteria femoralis into the abdominal aorta for the direct measurement of the arterial blood pressure.

The ECG was traced with subcutaneous insertion electrodes.

During the preparation of the animal and during the entire test period the rats were fixed on an electrically heated and thermostated operating table.

Procedure

The test substances were always introduced by intravenous injection, with an injection volume, per injection, of 1 ml/kg body weight. In intervals of 10 min each, doses increasing from 0.01 to 30 mg of the test substances were intravenously injected. In this way does effect curves for the measured parameters for the investigated substances were obtained.

From the measure data, using a regression calculation, equipotent doses for the positively inotropic effect $\Delta(dp/dt)_{60}$ were calculated. In addition, as criterion for the effectiveness of the substances, the maximum effect obtained maximal increase of $(dp/dt)_{60}$ and its corresponding does were determined. The table that follows shows the equipotent

TABLE OF RESULTS

| Substance (Example) | $DE_{1.5\ mHg/sec}$ mg/kg i.v. | W max mHg/sec |
|---|---|---|
| 1 | 0,01 | 3,7 |
| 1(a) | 0,96 | 2,4 |
| 1(b) | <1,0 | 3,5 |
| 1(c) | 0,29 | 2,5 |
| 1(e) | 0,07 | 3,9 |
| 1(f) | 1,21 | 4,3 |
| 1(h) | 0,20 | 3,3 |
| 2 | 1,14 | 4,1 |
| 3 | >10 | 1,4 |
| 4 | 0,03 | 4,9 |
| 5(a) | 0,02 | 4,4 |
| 5(b) | 0,06 | 4,6 |
| 5(c) | 0,06 | 4,5 |
| 5(d) | 0,39 | 4,0 |
| 8 | 0,09 | 4,2 |
| 9 | — | 0,9 | doses ($DE_{1.5}$ = the dose in mg/kg that leads to an increase of $(dp/dt)_{60}$ of 1.5 mHg/sec) and the maximal effectiveness ($W_{max}$ = the maximal increase of $(dp/dt)_{60}$.

It will be understood that the specification and examples are illustrative but not limitative of the present invention and that other embodiments within the spirit and scope of the invention will suggest themselves to those skilled in the art.

What is claimed is:

1. A compound of the formula

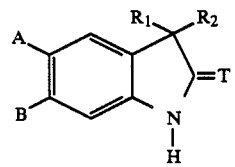

wherein
$R_1$ is hydrogen, $C_1$-$C_6$ alkyl, $C_2$-$C_6$ alkenyl or $C_3$-$C_7$ cycloalkyl,
$R_2$ is hydrogen, $C_1$-$C_6$ alkyl or $C_2$-$C_6$ alkenyl,
A is hydrogen, amino, nitro or Py—X—CO—NH— and
B is hydrogen, amino, nitro or Py—X—CO—NH—, in which X is a valency bond and Py is 2-, 3-, or 4-pyridyl which optionally carries oxygen on the righ hetero atom and can be optionally substituted with at least one member selected from the group consisting of $C_1$-$C_6$ alkyl, $C_1$-$C_6$ alkoxy, hydroxyl, cyano, nitro or halogen, and
T is oxygen or sulphur; with the proviso that either A or B is Py—X—CO—NH— and A and B are not simultaneously Py—X—CO—NH.

2. The compound of claim 1, wherein $R_1$ is hydrogen, $C_1$-$C_6$ alkyl or $C_3$-$C_7$ cycloalkyl.

3. The compound of claim 1, wherein $R_2$ is hydrogen or $C_1$-$C_6$ alkyl.

4. The compound of claim 1, wherein $R_1$ is hydrogen, methyl, ethyl, 2-methylpropyl or cyclopentyl, $R_2$ is hydrogen, methyl or ethyl.

5. The compound of claim 1, wherein T is oxygen.

6. The compound of claim 1, wherein A is hydrogen.

7. The compound of claim 1, wherein B is hydrogen.

8. The compound of claim 1, wherein A is hydrogen, amino, nitro or Py—X—CO—NH— and B is hydrogen, amino, nitro or Py—X—CO—NH—, in which X is a valency bond, and Py is a pyridyl-N-oxide and/or pyridyl optionally substituted by $C_1$-$C_6$ alkoxy, $C_1$-$C_6$ alkyl, hydroxyl or halogen, and T is oxygen.

9. The compound of claim 1, wherein X is a valency bond and Py is 2-, 3- or 4- pyridyl which optionally carries oxygen on the ring hetero atom.

10. The compound of claim 1 designated 3,3-dimethyl-5-(4-pyridinoylamino)-indolin-2-one.

11. The compound of claim 1 designated 3,3-dimethyl-6-(4-pyridinoylamino)-indolin-2-one.

12. The compound of claim 1 designated 3,3-dimethyl-6-nitro-5(4-pyridinoylamino)-indolin-2-one.

13. The compound of claim 1 designated 3,3-dimethyl-5-nitro-6(4-pyridinoylamino)-indolin-2-one.

* * * * *

UNITED STATES PATENT AND TRADEMARK OFFICE
CERTIFICATE OF CORRECTION

PATENT NO. : 4,963,686

DATED : October 16, 1990

INVENTOR(S) : Hölch et al.

It is certified that error appears in the above-identified patent and that said Letters Patent is hereby corrected as shown below:

Col. 1, after line 12: insert

-- The new pyrrolobenzimidazoles according to the present invention are compounds of the general formula:

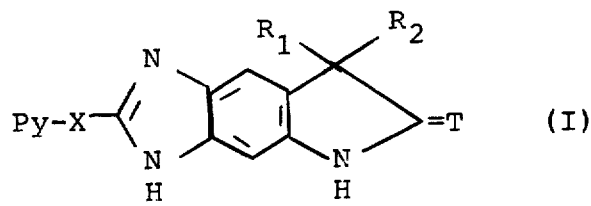

wherein $R_1$ is a hydrogen atom or an alkyl, alkenyl or cycloalkyl radical, $R_2$ is a hydrogen atom, an alkyl or alkenyl radical or a cyano group or a carbonyl group substituted by a hydroxyl or hydrazino group or by an alkyl, alkoxy, amino, alkylamino or dialkylamino group or together with $R_1$ represents a cycloalkylene radical or $R_1$ and $R_2$ together form an alkylidene or cycloalkylidene radical, X is a valency bond, a $C_1$-$C_4$ alkylene radical or a vinylene radical, T is an oxygen or sulphur atom and Py is a 2-, 3- or 4-pyridyl radical which optionally carries an oxygen atom on the ring

UNITED STATES PATENT AND TRADEMARK OFFICE
CERTIFICATE OF CORRECTION

PATENT NO. : 4,963,686

DATED : October 16, 1990

INVENTOR(S) : Hölch et al.

It is certified that error appears in the above-identified patent and that said Letters Patent is hereby corrected as shown below:

| | |
|---|---|
| Col. 1, after line 12: Cont'd. | heteroatom and/or can be substituted one or more times by alkyl, alkoxy, hydroxyl, cyano or nitro, as well as by halogen; the tautomers thereof and the physiologically acceptable salts thereof with inorganic and organic acids. -- |
| Col. 1, line 13: | change "posses" to -- possess --. |
| Col. 5, line 47: | change "toluence" to -- toluene --. |
| Col. 10, line 27: | change "5,6-diamono" to -- 5,6-diamino --. |
| Col. 15, line 63: | change "7-ethoxygarbonyl" to -- 7-ethoxycarbonyl --. |
| Col. 16, line 25: | change "[b2,3-f]" to -- [2,3-f] --. |
| Col. 23, line 41: | change "5-isonicotinoylamino" to -- 6-isonicotinoylamino --. |
| Col. 10, line 30: | change "5,40 ,6" to --5' ,6--. |

UNITED STATES PATENT AND TRADEMARK OFFICE
CERTIFICATE OF CORRECTION

PATENT NO. : 4,963,686
DATED : October 16, 1990
INVENTOR(S) : Hölch et al.

It is certified that error appears in the above-identified patent and that said Letters Patent is hereby corrected as shown below:

Col. 27, line 29:           change "11.0 g." to -- 11.9 g. --.

Col. 27, line 46:           change "bemzimidazol" to
                            -- benzimidazol --.

Signed and Sealed this

Second Day of March, 1993

Attest:

STEPHEN G. KUNIN

Attesting Officer         Acting Commissioner of Patents and Trademarks